(12) United States Patent
Vaisberg et al.

(10) Patent No.: US 7,151,847 B2
(45) Date of Patent: Dec. 19, 2006

(54) IMAGE ANALYSIS OF THE GOLGI COMPLEX

(75) Inventors: Eugeni A. Vaisberg, Foster City, CA (US); Ge Cong, El Cerrito, CA (US); Hsien-Hsun Wu, San Jose, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 244 days.

(21) Appl. No.: 09/792,012

(22) Filed: Feb. 20, 2001

(65) Prior Publication Data

US 2002/0141631 A1 Oct. 3, 2002

(51) Int. Cl.
*G06K 9/00* (2006.01)
(52) U.S. Cl. ...................................... 382/133
(58) Field of Classification Search ........ 530/424–435; 435/173–182; 382/128, 133, 170
See application file for complete search history.

(56) References Cited

U.S. PATENT DOCUMENTS

| | | | |
|---|---|---|---|
| 4,818,710 A | 4/1989 | Sutherland et al. | |
| 4,922,092 A | 5/1990 | Rushbrooke et al. | |
| 4,959,301 A | 9/1990 | Weaver et al. | |
| 4,965,725 A | 10/1990 | Rutenberg | |
| 5,016,283 A | 5/1991 | Bacus et al. | 382/129 |
| RE34,214 E | 4/1993 | Carlsson et al. | |
| 5,281,517 A | 1/1994 | Bacus et al. | 435/6 |
| 5,287,272 A | 2/1994 | Rutenberg et al. | |
| 5,326,691 A | 7/1994 | Hozier | |
| 5,355,215 A | 10/1994 | Schroeder et al. | |
| 5,526,258 A | 6/1996 | Bacus | |
| 5,548,661 A | 8/1996 | Price et al. | |
| 5,655,028 A | 8/1997 | Soll | |
| 5,710,022 A | 1/1998 | Zhu et al. | 435/69.1 |
| 5,733,721 A | 3/1998 | Hemstreet, III et al. | |
| 5,741,648 A | 4/1998 | Hemstreet et al. | |
| 5,768,412 A | 6/1998 | Mitsuyama et al. | 382/173 |
| 5,776,748 A | 7/1998 | Singhvi et al. | |

(Continued)

FOREIGN PATENT DOCUMENTS

EP 0468705 1/1992

(Continued)

OTHER PUBLICATIONS

Micheael V. Boland et al. Automated Recognition of Patterns Characteristic of Subcellular Structures in Fluorescence Microscopy Images. Rapid Communications. 1998, cytometry 33:366-375.*

(Continued)

*Primary Examiner*—Samir Ahmed
*Assistant Examiner*—Brian Le
(74) *Attorney, Agent, or Firm*—Beyer Weaver & Thomas, LLP

(57) ABSTRACT

Methods, code and apparatus analyze cell images to automatically identify and characterize the Golgi complex in individual cells. This is accomplished by first locating the cells in the image and defining boundaries of those cells that subsume some or all of the Golgi complex of those cells. The Golgi complex in the images typically have intensity values corresponding to the concentration of a Golgi component in the cell (e.g. a polysaccharide associated with the Golgi complex). The method/system then analyzes the Golgi components of the image (typically on a pixel-by-pixel basis) to mathematically characterize the Golgi complex of individual cells. This mathematical characterization represents phenotypic information about the cells' Golgi complex and can be used to classify cells. From this information, mechanism of action and other important biological information can be deduced.

40 Claims, 13 Drawing Sheets

U.S. PATENT DOCUMENTS

| | | | |
|---|---|---|---|
| 5,777,888 A | 7/1998 | Rine et al. | |
| 5,790,692 A | 8/1998 | Price et al. | |
| 5,790,710 A | 8/1998 | Price et al. | |
| 5,804,436 A | 9/1998 | Okun et al. | |
| 5,856,665 A | 1/1999 | Price et al. | |
| 5,893,095 A | 4/1999 | Jain et al. | |
| 5,919,646 A | 7/1999 | Okun et al. | |
| 5,932,872 A | 8/1999 | Price | |
| 5,962,520 A | 10/1999 | Smith et al. | |
| 5,976,825 A | 11/1999 | Hochman | |
| 5,985,549 A | 11/1999 | Singer et al. | 435/6 |
| 5,989,835 A | 11/1999 | Dunlay et al. | |
| 5,991,028 A | 11/1999 | Cabib et al. | |
| 5,995,143 A | 11/1999 | Price et al. | |
| 6,007,996 A | 12/1999 | McNamara et al. | |
| 6,008,010 A | 12/1999 | Greenberger et al. | |
| 6,078,681 A | 6/2000 | Silver | 382/133 |
| 6,083,763 A | 7/2000 | Balch | |
| 6,103,479 A | 8/2000 | Taylor | |
| 6,146,830 A | 11/2000 | Friend et al. | |
| 6,169,816 B1 | 1/2001 | Ravkin | 382/128 |
| 6,222,093 B1 | 4/2001 | Marton et al. | |
| 6,345,155 B1 | 2/2002 | Tojo et al. | |
| 6,615,141 B1 | 9/2003 | Sabry et al. | 702/19 |
| 6,658,143 B1 | 12/2003 | Hansen et al. | 382/133 |
| 2002/0141631 A1 | 10/2002 | Vaisberg et al. | |
| 2002/0154798 A1 | 10/2002 | Cong et al. | |

FOREIGN PATENT DOCUMENTS

| | | |
|---|---|---|
| EP | 0317139 | 4/1998 |
| EP | 0902394 | 3/1999 |
| WO | WO 87/02802 | 5/1987 |
| WO | WO 93/21511 | 10/1993 |
| WO | WO 95/10036 | 4/1995 |
| WO | WO 95/22749 | 8/1995 |
| WO | WO 96/01438 | 1/1996 |
| WO | WO 96/09605 | 3/1996 |
| WO | WO 97/11094 | 3/1997 |
| WO | WO 97/20198 | 6/1997 |
| WO | WO 97/40055 | 10/1997 |
| WO | WO 97/43732 | 11/1997 |
| WO | WO 97/45730 | 12/1997 |
| WO | WO 98/05959 | 2/1998 |
| WO | WO 98/35256 | 8/1998 |
| WO | WO 98/38490 | 9/1998 |
| WO | WO 98/44333 | 10/1998 |
| WO | WO 98/45704 | 10/1998 |
| WO | WO 99/05323 | 2/1999 |
| WO | WO 99/08091 | 2/1999 |
| WO | WO 99/17116 | 4/1999 |
| WO | WO 99/39184 | 8/1999 |
| WO | WO 99/44062 | 9/1999 |
| WO | WO 99/54494 | 10/1999 |
| WO | WO 99/67739 | 12/1999 |
| WO | WO 00/03246 | 1/2000 |
| WO | WO 00/06774 | 2/2000 |
| WO | WO 00/17624 | 3/2000 |
| WO | WO 00/17643 | 3/2000 |
| WO | WO 00/17808 | 3/2000 |
| WO | WO 00/26408 | 5/2000 |
| WO | WO 00/29984 | 5/2000 |
| WO | WO 00/31534 | 6/2000 |
| WO | WO 00/33250 | 6/2000 |
| WO | WO 00/43820 | 7/2000 |
| WO | WO 00/49540 | 8/2000 |
| WO | WO 00/50872 | 8/2000 |
| WO | WO 00/60356 | 10/2000 |
| WO | WO 00/65472 | 11/2000 |
| WO | WO 00/70528 A2 | 11/2000 |
| WO | WO0135072 A2 | 5/2001 |
| WO | WO 02/50512 A2 | 6/2002 |

OTHER PUBLICATIONS

Wang et al. Immunolocalization of 6. His-tagged pr in CHO cells with anti-His antibodies, Dec. 1999.*

U.S. Appl. No. 60/120,801, filed Feb. 19, 1999, Wang et al.

U.S. Appl. No. 60/142,646, filed Jul. 6, 1999, Boyce et al.

U.S. Appl. No. 60/142,375, filed Jul. 6, 1999, Boyce et al.

U.S. Appl. No. 60/108,291, filed Nov. 13, 1998, Boyce et al.

U.S. Appl. No. 60/110,643, filed Dec. 1, 1998, Smith.

U.S. Appl. No. 60/140,240, filed Jun. 21, 1999, Dunlay et al.

Printout from Q3DM Website (www.Q3DM.com), printed on Mar. 1, 2001, 30 Pages.

Montironi R., et al., "Computed Cell Cycle and DNA Histogram Analyses in Image Cytometry in Breast Cancer", Journal of Clinical Pathology, GB, London, vol. 46, No. 9, Sep. 1993, pp. 795-800.

Giuliano K.A., et al., "Fluorescent-Protein Biosensors: New Tools for Drug Discovery", Trends in Biotechnology, GB, Elsevier Publications, Cambridge, vol. 16, No. 3, Mar. 1998, pp. 135-140.

Printout from Automated Cell Website (www.automatedcell.com) printed on Mar. 9, 2001, 24 Pages.

Ravi Kapur, et al., "Design and Fabrication of Spatially Controlled Miniaturized Organ Systems From Stem Cells", U.S. Appl. No.: 60/127,339, filed Apr. 1, 1999, 21 Pages.

Giuliano et al., "High-Content Screening: A New Approach to Easing Key Bottlenecks in the Drug Discovery Process", *J. Biomolecular Screening*, 2(4): 249 (1997).

Pauwels et al., "Determination of the Mechanism of Action of Anticancer Drugs by Means of the Computer-Assisted Microscope Image Analysis of Feulgen-Stained Nuclei", *J.Pharmacological and Toxicological Methods*. 37: 105-115 (1997).

Pauwels et al., "Monitoring Of Chemotherapy-Induced Morphonuclear Modifications By Means Of Digital Cell-Image Analysis", *I. Cancer Res. Clin. Oncol.*, 119: 533-540 (1993).

Pauwels et al., "In Vitro Digital Cell Image Analysis of Morphonuclear Modifications Induced by Natural DNA- Interacting Anticancer Drugs in Three Neoplastic Cell Lines", *Meth. Find. Exp. Clin. Pharmacol* . . . 17(3): 151-161 (1995).

Pauwels et al., "The Application of Computerized Analysis of Nuclear Images and Multivariate Analysis to the Understanding of the Effects of Antineoplastic Agents and Their Mechanism of Action", *Meth. Find. Exp. Clin.* Pharmacol, 15(2): 113-124 (1993).

Teri Adams, et al., "Cell Patterning on Glass and Polymeric Substrates", U.S. Appl. No.: 60/127,138,119, filed Jun. 7, 1999, 21 Pages.

Pauwels et al., "Combination of Computerized Morphonuclear and Multivariate Analyses to Characterize In Vitro the Antineoplastic Effect of Alkylating Agents", J. Pharmacol. and Toxicol. Methods, 33(1): 34-45 (1995).

Weinstein et al., "An Information-Intensive Approach to the Molecular Pharmacology of Cancer", *Science,* 275: 43-349 (Jan. 17, 1997).

Pauwels et al., "Determination of the Mechanism of Action of Anticancer Drugs by Means of the Computer-Assisted Microscope Image Analysis of Feulgen-Stained Nuclei", J. Pharmacological and Toxicological Methods. 37: 105-115 (1997).

Rubas, et al., "An Integrated Method to Determine Epithelial Transport and Bioactivity of Oral Drug Candidates *in Vitro*," Pharmaceutical Research, vol. 13, No. 1, (1996) pp. 23-27.

Sunblad et al., "The use of image analysis and automation for measuring mitotic index in apical confier meristems", © Oxford University Press 1998, Journal of Experimental Botany, vol. 49, No. 327, pp. 1749-1756.

Uria JA, et al., "Regulation of Collagenase-3 Expression in Human Breast Carcinomas in Mediated by Stromal-Epithelial Cell Interactions", Cancer Res 1997 Nov. 1;57 (21):4882-8, Abstract.

Cseke, I., "A Fast Segmentation Scheme for White Blood Cell Images" (1992) IEEE, pp. 530-533.

Serbouti, S., et al., "Image Segmentation and Classification Methods to Detect Leukemias", (1991) Annual Int'l Conf. of IEEE Eng. In Medicine & Biology Soc., vol. 13, No. 1, pp. 0260-0261.

Cormack, Brendan P. et al., "FACS-optimized mutants of the green fluorescent protein (GFP)", 1996, *Gene*, vol. 173, pp. 33-38.

Craig, Elizabeth and Gross, Carol, "Is hsp70 the cellular thermometer?", 1991, *TIBS*, pp. 135-140.

Cubitt, Andrew B. et al., "Understanding, improving and using green fluorescent proteins", 1995, *TIBS*, vol. 20, pp. 448-455.

Dobson, Stephen P., "Dynamics of insulin-stimulated translocation of GLUT4 in single living cells visualized using green fluorescent protein", 1996, *FEBS Letters*, vol. 393, pp. 179-184.

Georget, V., et al., "Trafficking of the androgen receptor in living cells with fused green fluorescent protein—androgen receptor", 1997, *Molecular and Cellular Endocrinology*, vol. 129, pp. 17-26.

Lippincott-Schwartz, Jennifer and Smith, Carolyn L., "Insights into secretory and endocytic membrane traffic using green fluorescent protein chimeras", 1997, *Current Opinion in Neurobiology*, vol. 7, pp. 631-639.

Misteli, Tom and Spector, David L., "Applications of the green fluorescent protein in cell biology and biotechnology", 1997, *Nature Biotechnology*, vol. 15, pp. 961-964.

Palm, Gottfried J. et al., "The structural basis for spectral variations in green fluorescent protein", 1997, *Nature Structural Biology*, vol. 4, No. 5, pp. 361-365.

Sakai, Kenji et al., "Purification and characterization of N-acyl-D-glutamate deacylase from *Alcaligenes xylosoxydans* subsp. *xylosoxydans* A-6", 1991, *FEBS Letters*, vol. 289, No. 1, pp. 44-46.

Shulga, Nataliya et al., "In Vivo Nuclear Transport Kinetics in *Saccharamyces cerevisiae*: A Role for Heat Shock Protein 70 during Targeting and Translocation", 1996, *The Journal of Cell Biology*, vol. 135, No. 2, pp. 329-339.

Tarasova, Nadya I. et al., "Visualization of G Protein-coupled Receptor Trafficking with the Aid of the Green Fluorescent Protein", 1997, *The Journal of Biological Chemistry*, vol. 272, No. 23, Issue of Jun. 6, pp. 14817-14824.

Welsh, Stephen and Kay, Steve A., "Reporter gene expression for monitoring gene transfer", 1997, *Current Opinion in Biotechnology*, vol. 8, pp. 617-622.

D.L. Taylor, "The new vision of light microscopy", American Scientist 80:322-335, 1992.

K. A. Giuliano et al., "Measurement and manipulation of cytoskeletal dynamics in living cells", Current Opinion in Cell Biology 7:4-12, 1995.

BioDx, Internet Archive Way-Back Machine, Feb. 4, 1997 From website www.biodx.com.

A. Waggoner et al., "Multiparameter Fluorescence imaging microscopy: re-agents and instruments" Human Pathology, vol. 27, No. 5, 494-502, 1996.

Benveniste et al., "Characterization of Internalization and endosome formation of epidermal growth factor in transfected NIH-3T3 cells by computerized image-intensified three-dimensional fluorescence microscopy", The Journal of Cell Biology 109: 2105-2115, 1989.

K.L. Carey et al., "Evidence using a green fluorescent protein-glucocorticoid receptor chimera that the RAN/TC4 GTPase mediates an essential function independent of nuclear protein import", The Journal of Cell Biology, vol. 133, No. 5, 985-996, 1996.

J. Kolega et al., "Quantitaion of cytoskeletal fibers in fluorescence images stress fiber disassembly accompanies dephosphorylation of the regulatory light chains of myosin II", Bioimaging 1:136-150, 1993.

D.L Farkas et al., "Multimode light microscopy and the dynamics of molecules, cells, and tissues", Annu. Rev. Physiol. 55:785-817, 1993.

W. Böcker et al., Automated cell cycle analysis with fluorescent microscopy and image analysis, Phys. Med. Biol. 41:523-537, 1996.

R. Pepperkok et al., "System for quantitation of gene expression in single cells by computerized microimaging: Application to c-*fos* expression after microinjection of anti-casein kinase II antibody", Experimental Cell Research 204:278-285, 1993.

F. Hanakam, "Myristoylated and non-myristoylated forms of the pH sensor protein hisactophilin II: intracellular shuttling to plasma membrane and nucleus monitored in real time by a fusion with green fluorescent protein", The EMBO Journal 15(12):2935-43, 1996.

N.B. Cole, "Golgi Dispersal during microtubule disruption: Regeneration of Golgi stacks at Peripheral Endoplasmic Reticulum Exit sites," Molecular Biology of the Cell, vol. 7, 631-650, 1996.

B.M. Machiels Subcellular localization of proteasomes in apoptotic lung tumor cells and persistence as compared to intermediate filaments European Journal of Cell Biology 70:250-259, 1996.

N. Yasuhara et al., "Essential Role of active nuclear transport in apoptosis" Genes to Cells 2:55-64, Jan. 1997.

BioDx, Inc., Internet archive, way back machine May 21, 1997 From website www.biodx.com.

M.V. Rogers, "Light on high -throughput screening: fluorescence-based assay technologies", Drug Discovery Today, vol. 2, No. 4, 156-160 Apr. 1997.

W. Böcker et al., "Image Processing algorithms for the automated micronucleus assay in binucleated human lymphocytes", Cytometry 19:283-294 (1995).

Lansing D. Taylor, U.S. Provisional application No. 60/018,696, filed May 30, 1996.

Taylor et al., "Automated Interactive Microscopy: Measuring and Manipulating the Chemical and Molecular Dynamics of Cells and Tissues," Intl. Soc. for Optical Engineering 2678: 15-27 (1996).

Schroder et al., "FLIR: A new instrument for accurate, high throughput optical screening," Journal of Biomolecular Screening, vol. 1, No. 2, 1996, pp. 75-80.

Mattheakis et al., PCT Search Report for Int'l Application No. PCT/US2004/022970, Int'l Filing Date Jul. 15, 2004, dated Dec. 1, 2004.

Mattheakis et al., PCT Written Opinion for Int'l Application No. PCT/US2004/022970, Int'l Filing Date Jul. 15, 2004.

Towner et al., "Non-Invasive in Vivo Magnetic Resonance Imaging Assessment of Acute Aflatoxin B1 Hepatotoxicity in Rats", BBA-General Subjects, Elsevier Science Publishers, NL, vol. 1475, No. 3, Jul. 26, 2000, pp. 314-320.

Sturgeon et al., "In Vivo Assessment of Microcystin-LR-induced Hepatoxicity in the rat using proton nuclear magnetic rezsonance ($^1$H-NMR) Imaging" BBA- General Subjects, Biochemica et Biophysica Acta 1454 (1999) pp. 227-235.

Sakai et al., Rapid and Sensitive Neurotoxicity Test Based on the Morphological Changes of PC12 Cells with Simple Computer-Assisted Image Analysis, Journal of Bioscience and Bioengineering, vol. 90, No. 1, 20-24. 2000.

Hall et al., "Two Methods of Assessment of Methotrexate Hepatotoxicity in Patients with Rheumatoid Arthritis", Annals of the Rheumatic Diseases 1991, vol. 50, No. 7, pp. 471-476.

Molinari et al., "Automated Image Analysis for Monitoring Oxidative Burst in Macrophages", Analytical and Quantitative Cytology and Histology, vol. 22, No. 5, Oct. 2000, pp. 423-427.

Russ, J.C., "The Image Processing Handbook," Second Edition, Boca Raton: CRC Press, 1995, pp. 169-474 and 457-461.

Lu et al., "Hierarchical Shape Recognition Using Polygon Approximation and Dynamic Alignment," IEEE Paper CH2561-9, vol. 2, pp. 976-979, 1988.

U.S. Appl. No. 60/127,339, filed Apr. 1, 1999, Kapur et al.

U.S. Appl. No. 60/138,119, filed Jun. 7, 1999, Adams et al.

Hofland et al., "Role of Tumor-Derived Firbroplats in the Growth of Primary Cultures of Human Breast-Cancer Cells: Effects of Epidermal Growth Factor and the Somatostatin Analogue Octreotide". Int. J. Cancer; 60, 93-99 (1995).

Stearns et al., "Interleukin 10 (IL-10) Inhibition of Primary Human Prostate Cell-induced Angiogenesis: IL-10 Stimulation of Tissue Inhibitor of Metalloproteinase-1 and Inhibition of Matrix Metalloproteinase (MMP)-2/MMP-9 Secretion". Clinical Cancer Research, vol. 5, 189-196, Jan. 1999.

Takayama et al., "Patterning cells and their environments using multiple laminar fluid flows in a capillary networks". Proc. Natl. Acad. Sci., USA, vol. 96, pp. 5545-5548, May 1999. XP-002159130.

Hartwell et al., "Integrating Genetic Approaches into the Discovery of Anticancer Drugs". Science, vol. 278, Nov. 7, 1997. XP002916842.

Ng et al, "Evaluating Multi-Dimensional Indexing Structures for Images Transformed by Principal Component Analysis". Dept. of Computer Science, University of British Colombia, Vancouver, B.C. V6T 1Z4, Canada. XP000642562.

Boland et al. "Automated Recognition of Patterns Characteristics of Subcellular Structures in Fluorescence Microscopy Images". Cytometry 33:366-375 (1998).

* cited by examiner

IMAGE ANALYSIS OF THE GOLGI COMPLEX

CROSS-REFEERNCE TO RELATED PATENT APPLICATIONS

This application is a CIP of 09/729,754 now U.S. Pat. No. 6,876,760 issued Apr. 5, 2005 which in turn is a CIP of 09/310,879 filed May 14, 1999; 09/311,996 filed May 14, 1999; and of 09/311,890 filed May 14, 1999 now Pat. No. 6,743,576, issued Jun. 1, 2004.

BACKGROUND OF THE INVENTION

The present invention relates to methods and apparatus for characterizing a cell's condition based upon the state of its Golgi organelle. More specifically, the invention relates to image analysis methods and apparatus that rapidly characterize a cell based upon phenotypic characteristics of its Golgi complex.

The Golgi complex is a central and complex organelle within eukaryotic cells. It is involved in the sorting, modifying, and transporting of cellular molecules. It plays important roles in intracellular processes including endocytosis, exocytosis, and transport between cellular organelles. A detailed discussion of the role of the Golgi complex in cellular processes can be found in various treatises on cell biology. One example is Alberts et al. "Molecular Biology of the Cell" Garland Publishing, Inc., which is incorporated herein by reference for all purposes.

The Golgi complex can be an important indicator of the cellular effects caused by certain external agents. As a phenotypic characteristic, the Golgi complex has considerable value in drug discovery and fundamental biological research. For example, certain drugs and genetic modifications subtly affect transport pathways within a cell in ways that are manifest by the Golgi condition. Unfortunately, the value of the Golgi complex as an indicator has not been fully realized. This is because no simple consistent technique has been developed for characterizing the condition of Golgi complex in a high throughput manner.

SUMMARY OF THE INVENTION

This invention addresses the above need by providing methods, code and apparatus that analyze cell images to automatically identify and characterize Golgi in individual cells. The invention accomplishes this by first locating the cells in the image and defining subregions of those cells that subsume some or all of the Golgi of those cells. The Golgi complex in the images typically have intensity values corresponding to the concentration of a Golgi component in the cell (e.g. a polysaccharide associated with the Golgi complex). The method/system then analyzes the Golgi components of the image to mathematically characterize the Golgi complex of individual cells. This mathematical characterization represents phenotypic information about the cells' Golgi complex and can be used to infer biological/physiological state of cells. From this information, mechanism of action and other important biological information can be deduced.

One aspect of this invention pertains to a method of analyzing an image of one or more cells. This method may be characterized by the following sequence of operations (typically implemented on a computing device): (a) identifying a region of the image subsuming some or all of the Golgi complex of a single cell; (b) within this region, automatically identifying the location of the Golgi complex; and (c) automatically mathematically characterizing the Golgi complex within the single cell. Preferably, the mathematical characterization is based upon (i) the Golgi complex location within the region and/or (ii) the concentration of a Golgi component within the region, In addition to a basic characterization of the Golgi complex, which typically involves some basic morphological or statistical characterization, the process may automatically classify the Golgi complex in a category that at least partially distinguishes between normal Golgi and Golgi that is either diffuse or disperse or both diffuse and disperse. Such classification may be accomplished using a biological model, in the form of a neural network or regression model (e.g. a CART), for example.

Regarding the operation of identifying the region of the image subsuming some or all of the Golgi complex, the process may "segment" the image into multiple regions, each subsuming at least part of an individual cell. In a one example, segmentation involves identifying locations of nuclei in the cells, and then dilating the locations of the nuclei to subsume the locations of some or all of the Golgi complex.

Many different mathematical characterizations of the Golgi complex may be made. Preferably, all of them have biological relevance. Examples of types of mathematical characterizations include (i) an indicator of the peakedness of a histogram of at least one component of the Golgi complex, (ii) the texture of the Golgi complex and (iii) and the amount of Golgi complex in the region. As specific examples, the mathematical characterization of the Golgi complex include the kurtosis of intensity values obtained from the image, eigenvalues of a singular value decomposition of intensity values obtained from the image, and at least one of a mean and a standard deviation of intensity values obtained from the image.

Another aspect of this invention pertains to apparatus for automatically analyzing an image of one or more cells. Such apparatus may be characterized by the following features: (a) an interface configured to receive the image of one or more cells; (b) a memory for storing, at least temporarily, some or all of the image; and (c) one or more processors in communication with the memory and designed or configured to segment the image into discrete regions, each subsuming some or all of the Golgi complex in single cell. The processors may additionally characterize the Golgi complex of single cells by operating on the discrete regions. Still further, the processors may be designed or configured to classify the Golgi complex based upon such characterization of the Golgi complex. In one example, the classification distinguishes between normal Golgi and Golgi that is diffuse or disperse. The classification may make use of a biological model, in the form of a classification and regression tree, for example.

Still another aspect of the invention pertains to methods of producing a model for classifying cells based upon the condition of Golgi within the cells. Such method may be characterized by the following sequence: (a) receiving images of a plurality of cells of a training set; (b) analyzing the images to mathematically characterize the Golgi within the multiple cells from the training set; and (c) applying a modeling technique to the mathematical characterizations obtained in (b) to thereby produce the model. Typically, the training set will contain individual cells having Golgi in various states. The various states of Golgi in the cells of the training set may be produced, at least in part, by treatment with multiple exogenous agents such as drugs or drug candidates.

The process of analyzing the images mathematically may involve some of the operations outlined above such as segmentation, characterization, and classification. In one preferred approach, the modeling technique comprises generating a classification and regression tree.

Yet another aspect of the invention pertains to computer program products including machine-readable media on which are stored program instructions for implementing a portion of or an entire method as described above. Any of the methods of this invention may be represented, in whole or in part, as program instructions that can be provided on such computer readable media. In addition, the invention pertains to various combinations of data generated and/or used as described herein.

These and other features and advantages of the present invention will be described in more detail below with reference to the associated figures.

DETAILED DESCRIPTION OF INVENTION

A premise of this invention is that the shape and arrangement of Golgi in a cell provides valuable information about the cell's condition. If such condition results from treatment with a drug or other exogenous agent, then the Golgi complex may shed light on a mechanism of action.

In most normal cells, the Golgi complex is concentrated in a perinuclear region. In other words, normal Golgi is located in a cell's cytoplasm proximate to the nucleus. The chemical composition of the Golgi complex (and associated organelles and vacuoles) also affects the state of the Golgi within a cell's cytoplasm. Thus, when the particular drug or other exogenous agent affects a cell's cytoskeletal components and/or Golgi chemistry, this mechanism of action can be identified or suggested by examining the cell's Golgi complex.

In accordance with this invention, image analysis of the Golgi complex may be used to characterize the effects of any number of cellular stimuli. Stimuli of interest may include exposure to materials, radiation (including all manner of electromagnetic and particle radiation), forces (including mechanical, electrical, magnetic, and nuclear), fields, and the like. Examples of materials that may be used as stimuli include organic and inorganic chemical compounds, biological materials such as nucleic acids, carbohydrates, proteins and peptides, lipids, various infectious agents, mixtures of the foregoing, and the like. Other specific examples of agents include exposure to different temperatures, non-ambient pressure, acoustic energy, electromagnetic radiation of all frequencies, the lack of a particular material (e.g., the lack of oxygen as in ischemia), etc.

Figure 1A:
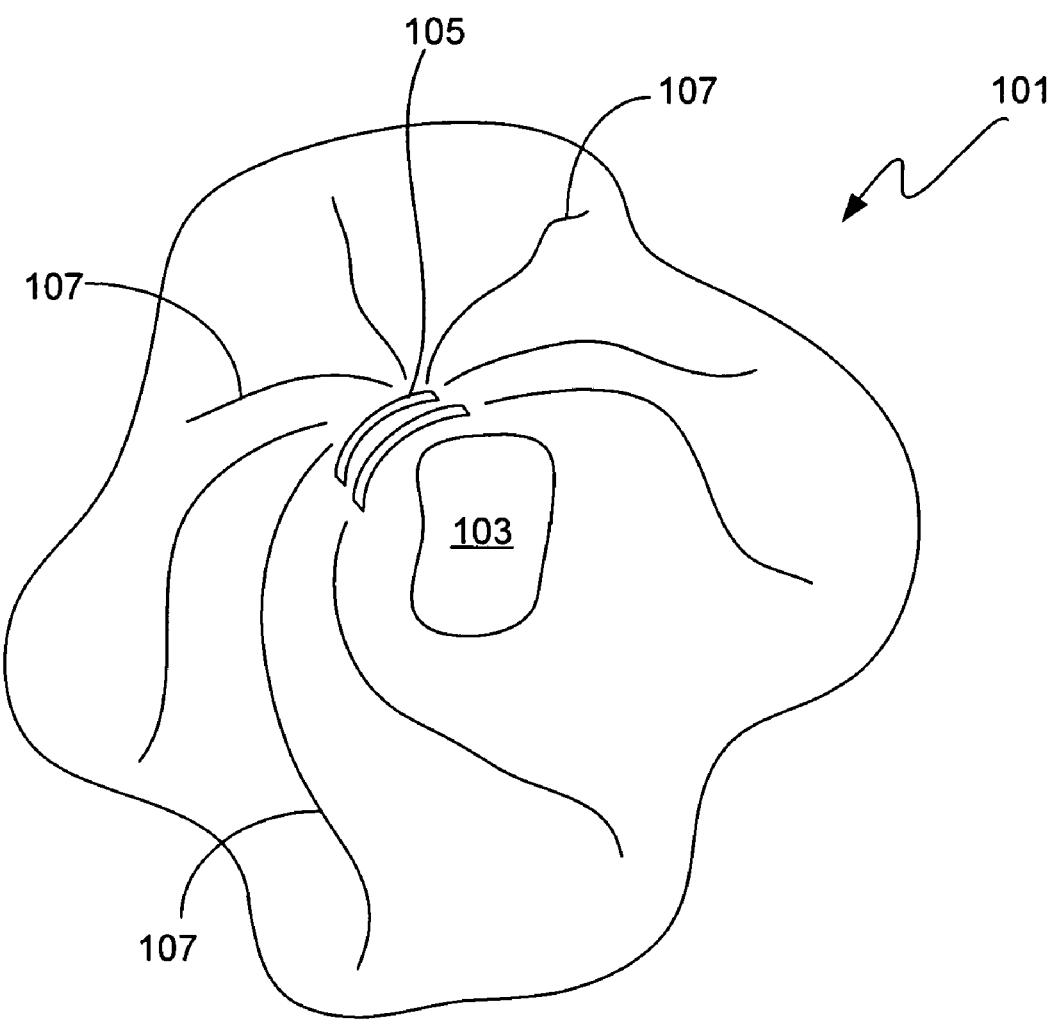
FIGS. 1A–1D depict, in cartoon fashion, cells having Golgi in normal, dispersion, diffusion, and diffusion/dispersion states, respectively.

Turning now to FIGS. 1A, 1B, 1C, and 1D, the Golgi complex may exist in four separate and identifiable end states. Other detectable end states may also exist. For purposes of illustration, however, this document will focus on the four states depicted in FIGS. 1A–1D. FIG. 1A depicts a cell in an interphase stage of the cell cycle. Many cells have Golgi generally located as depicted, so long as they are not experiencing a major perturbation. As shown, a cell 101 includes a nucleus 103 and the Golgi apparatus 105. In this "normal" cell, the Golgi complex lies close to the nucleus 103 primarily on one side of the nucleus. A region of the cell where the Golgi complex resides is also proximate to the microtubule organizing center (MTOC), a structure within the cells from which the microtubules 107 radiate. Normal localization and morphology of the Golgi complex 105 is mediated by, among other factors, microtubules 107 and microtubule motors, proteins that drive the motion of various cellular components along microtubules.

Figure 1B:
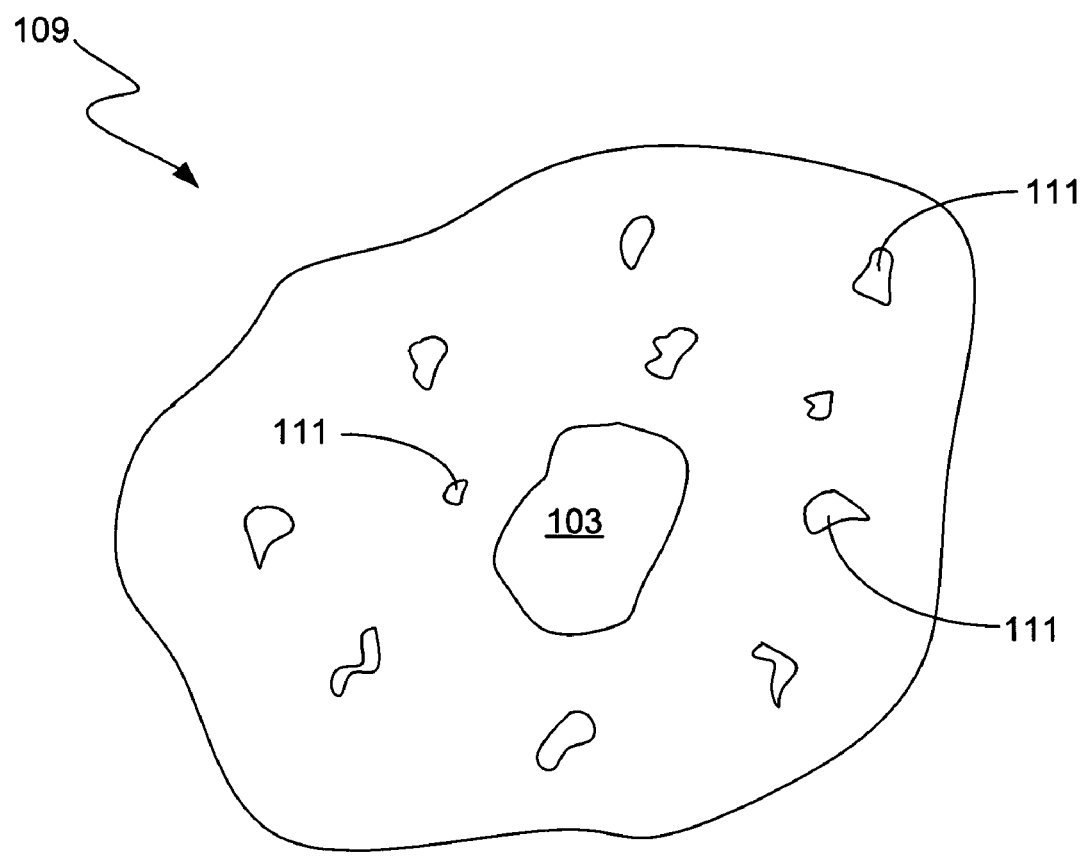

Some changes in physiological conditions of the cell might cause fragmentation of the Golgi apparatus. Golgi in this condition is said to be "disperse." FIG. 1B depicts, in cartoon fashion, a cell 109 in which Golgi fragments 111 are dispersed throughout the cytoplasm. This state of the Golgi complex may arise, for example, when the microtubule component of the cytoskeleton has been disrupted. Some drugs, for example, cause depolymerization of tubulin. When this occurs, the Golgi complex no longer remains confined to tight bands in the MTOC. Rather, it disperses throughout the cytoplasm as depicted in FIG. 1B. Other exogenous agents may disrupt microtubule motors. This too can cause dispersion of the Golgi complex. In general, exogenous agents that disrupt the microtubule cytoskeleton, either directly or indirectly, lead to dispersion of the Golgi complex.

Figure 1C:
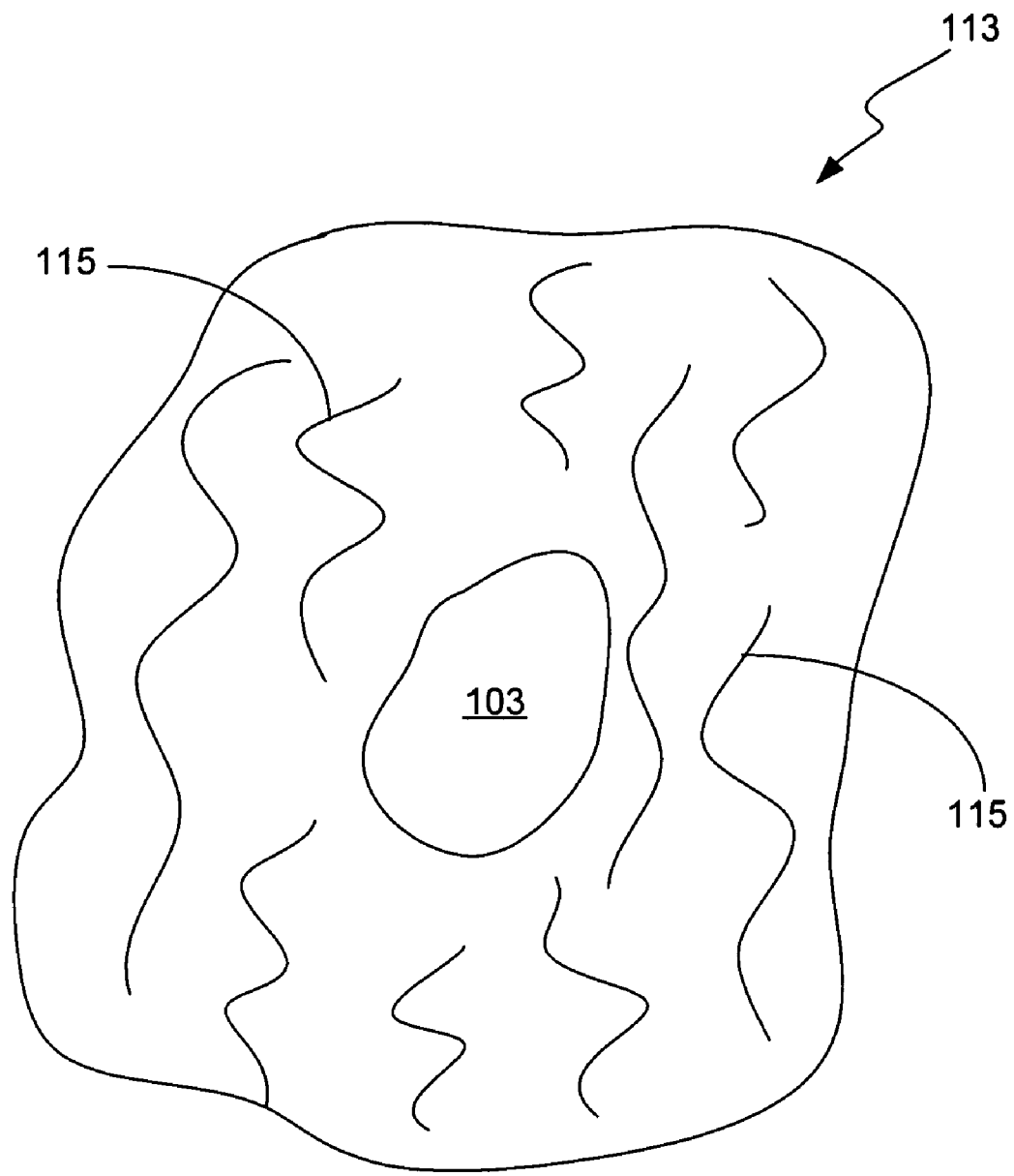

FIG. 1C depicts a third end state of the Golgi organelle. As shown there in cartoon fashion, a cell 113 has had its Golgi 115 spread throughout the cytoplasm without fragmentation. Here again the Golgi complex no longer remains confined to the perinuclear area. However, rather than forming discrete fragments it diffuses more or less evenly throughout the cells cytoplasm. Golgi in this condition is said to be in a "diffuse" state.

Golgi diffusion typically results when the dynamic barrier between the Golgi complex and endoplasmic reticulum compartments is disrupted to some degree. Actually, at this point, there may be no distinct Golgi. Rather the endoplasmic reticulum and Golgi have become one entity. This condition may result from a direct or indirect effect on the pathways between the endoplasmic reticulum and the Golgi complex. Any of a number of different exogenous and endogenous influences may cause this. In the end, the chemistry of the Golgi membrane changes significantly from its normal state.

Figure 1D:
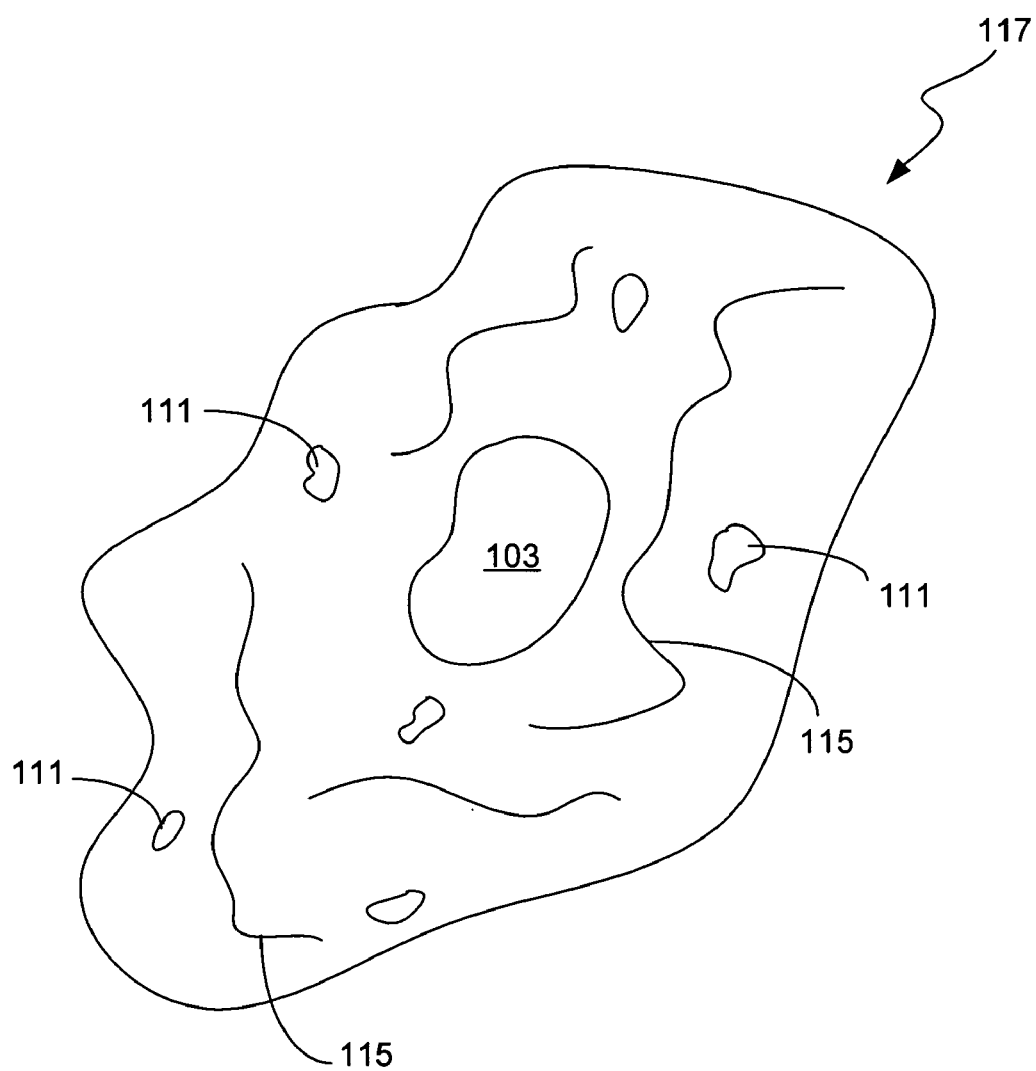

The various states depicted in FIGS. 1A–1C represent "end states" in which the Golgi complex has reached an extreme. Obviously, depending upon the level of an effect causing cell disruption, the Golgi complex may exist in any one of these states only to a limited degree. Thus, for example, a cell may exist may exist in a state between diffusion and dispersion as depicted in FIG. 1D. As shown there, a cell 117 includes both diffuse Golgi components 115 and disperse Golgi components 111. In preferred embodiments, this invention can determine the degree to which a particular cell resides in any one of the 4 states depicted in FIGS. 1A–1D.

Note also that the some of the influences may affect absolute amounts of Golgi components interacting with a particular Golgi marker. Some embodiments of this invention characterize the cell based upon the concentration of a marked Golgi component, which is affected by the degree to which an amount of a chemical constituent (or constituents) of the Golgi complex has changed from its normal state.

Note that the normal state depicted in FIG. 1A is normal only for interphase cells, not for mitotic cells. Golgi naturally becomes dispersed and/or diffuse during mitosis. When a large number of dividing cells are present, these effects can obscure detection of interesting changes to the Golgi complex that one might wish to detect. Therefore, the present invention may include operations that distinguish between mitotic and interphase cells. In the subsequent discussion, much of the characterization of the Golgi complex assumes that an algorithm has already limited consideration to interphase cells.

Preparation of the Image

Generally the images used as the starting point for the methods of this invention are obtained from cells that have been specially treated and/or imaged under conditions that contrast the cell's Golgi from other cellular components and the background of the image. In the preferred embodiment, the cells are fixed and then treated with a labeling agent (i.e., a marker) that binds to one or more Golgi components and shows up in an image. Preferably, the chosen agent specifically binds to cell components that are enriched in the Golgi complex. The agent should provide a strong signal to show where it is concentrated in a given cell. To this end, the agent may be luminescent, radioactive, fluorescent, etc. Various stains and fluorescent compounds may serve this purpose.

The Golgi complex has numerous components that can be marked for generating images for use with this invention. For example, the Golgi contains specific proteins, lipids, and polysaccharides that can be marked for analysis. Some of these components occur in much higher concentration within the Golgi complex than within other cellular components. In one preferred embodiment, the Golgi complex is identified using fluorescently labeled antibodies that bind specifically to a Golgi component. In a particularly preferred embodiment, the Golgi complex is identified by treatment with labeled Lens culinaris lectin (LC lectin). Lectins generally bind very specifically to certain polysaccharides. LC lectin binds to polysaccharide chains on proteins (protoglycans) having a N-acetyl-d-glucosearnine residue at the end of the polysaccharide chain. Alternatively one could use antibodies to proteins enriched in the Golgi complex, such as gp130, [beta]COP.

Various techniques for preparing and imaging appropriately treated cells are described in U.S. patent application Ser. Nos. 09/310,879, 09/311,996, and 09/311,890, previously incorporated by reference. In the case of cells marked with a fluorescent material, a collection of such cells is illuminated with light at an excitation frequency. A detector is tuned to collect light at an emission frequency. The collected light is used to generate the image and highlights regions of high Golgi component concentration.

Sometime corrections must be made to the measured intensity. This is because the absolute magnitude of intensity can vary from image to image due to non-linearities in the image acquisition procedure and/or apparatus. Specific optical aberrations can be introduced by various image collection components such as lenses, filters, beam splitters, polarizers, etc. Other non-linearities may be introduced by an excitation light source, a broad band light source for optical microscopy, a detector's detection characteristics, etc. For example, some optical elements do not provide a "flat field." As a result, pixels near the center of the image have their intensities exaggerated in comparison to pixels at the edges of the image. A correction algorithm may be applied to compensate for this effect. Such algorithms can be easily developed for particular optical systems and parameter sets employed using those imaging systems. One simply needs to know the response of the systems under a given set of acquisition parameters.

General Algorithms for Image Analysis

Various algorithms can be used to analyze cell images that highlight Golgi. Certain specific examples will be described herein. In general, much of the relevant information associated with Golgi can be obtained by specifically analyzing interphase cells and ignoring, or treating separately, mitotic cells. Preferably, algorithms of this invention identify the normal, diffuse, and disperse states of Golgi within interphase cells. To this end, the algorithm may obtain certain morphological and/or statistical information about the Golgi complex from the image and use that information to classify the Golgi.

Most images of relevance will depict the Golgi complex as variations in intensity over position in the image, with higher intensity regions in the image corresponding to regions of the cell where the Golgi component exists in relatively high concentrations. Examples of morphological and statistical image characteristics that can be used to effectively characterize the Golgi include the "peakedness" of a histogram of pixel intensities, the texture of the Golgi regions of the image, the overall or total intensity obtained in the image, and the moments of the Golgi complex about a nucleus identified in a cell image.

Often it will be desirable to use an image analysis algorithm for Golgi in conjunction with image analysis algorithms for other components of a cell. In fact, in a preferred algorithm described herein, it is necessary to first identify the nucleus of a cell prior to identifying the Golgi complex.

Figure 2:
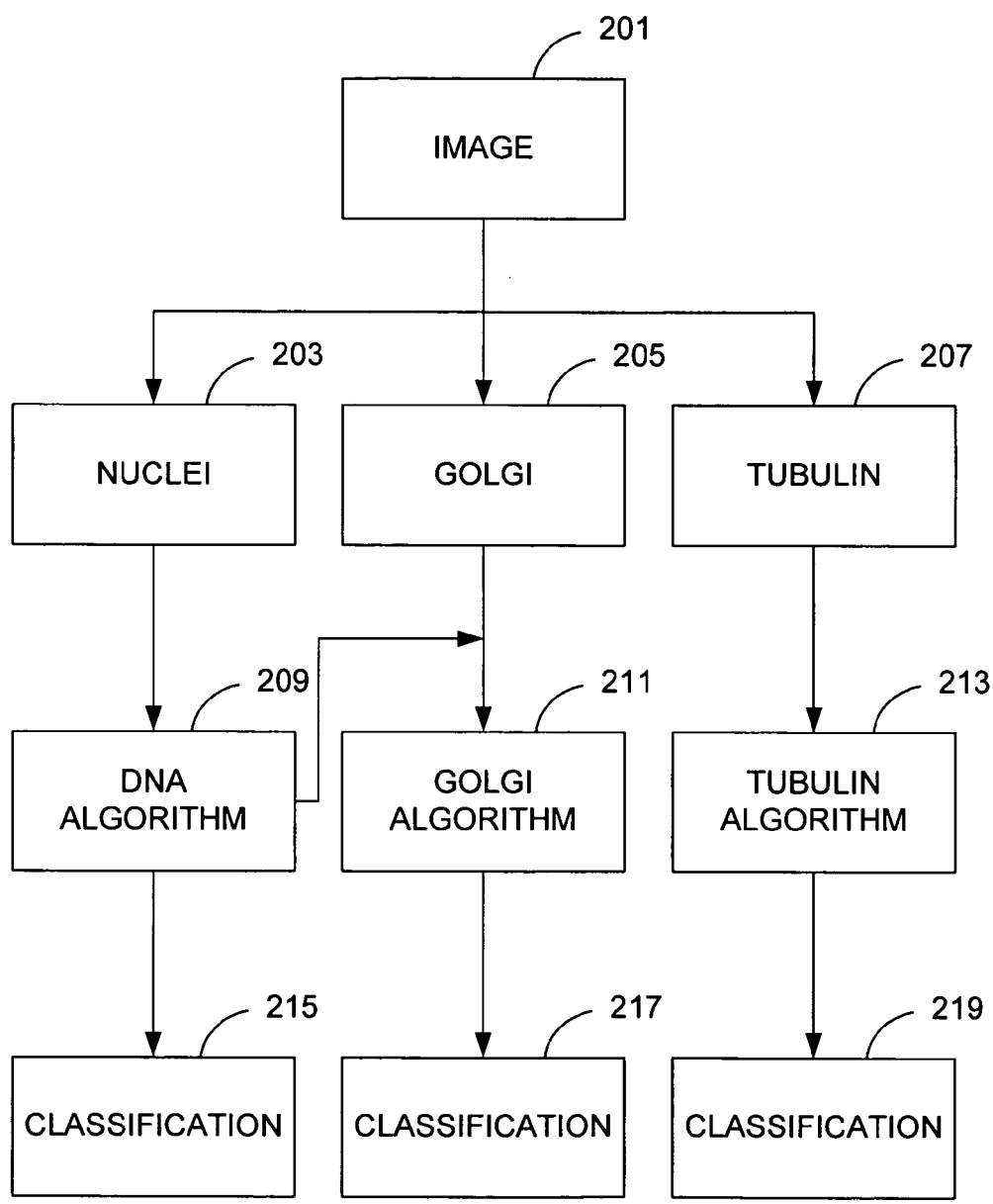
FIG. 2 is a block diagram of an architecture and data flow for using multiple image analysis algorithms, each handling a different image of a microscopic field.

FIG. 2 depicts, from a global perspective, an algorithm (or group of algorithms) that characterizes a cell in terms of its nuclei, Golgi, and tubulin. As shown in FIG. 2, a global image analysis 200 begins with one or more images 201 as input. In this example, image 201 possesses three separate "channels." Each of these channels represents a different label that can be separately captured by the imaging apparatus and represented distinctly in an image of the cell or a field of cells. In a typical example, the separate labels are separate fluorophores having distinct emission frequencies. In a very specific example, cells are treated with a marker for DNA emitting in blue, a marker for the Golgi complex emitting in green, and a marker for tubulin emitting in red.

As depicted in FIG. 2, the image analysis algorithm 200 includes separate process branches: a nuclei analysis branch 203, a Golgi analysis branch 205, a tubulin analysis branch 207.

Each of these branches has its own separate algorithm for analyzing the image. As shown, the nuclei are analyzed with an algorithm 209, the Golgi complex are analyzed with an algorithm 211, and the tubulin is analyzed with a algorithm 213. Each of these algorithms act on information taken from the channel specific to the cell component of interest. The output of each of these algorithms is the combination of extracted features and, possibly (not necessarily), a separate classification or characterization of the associated cell component according to its state in a particular cell. As depicted, the output of algorithm 209 is the combination of identified individual nuclei (this is the part of the output that is later used by the Golgi algorithm), their morphological and intensity features, and a classification of the cell based upon its DNA or nucleus features. In a preferred embodiment, block 215 classifies the cell based upon its stage in the cell cycle. The output of algorithm 211 are Golgi features which are input to 217 for classification. Preferably, this classification is based upon (1) the type of Golgi arrangement (e.g. the degree of diffusion, dispersion, and normalcy) and/or (2) the concentration of one or more Golgi components (depicted as intensity of signal emitted by one or more Golgi markers). Finally, the output of tubulin algorithm 213 is the tubulin features which are input to 219 for classification. In one embodiment, this classification characterizes the overall shape of a cell.

Figure 3:
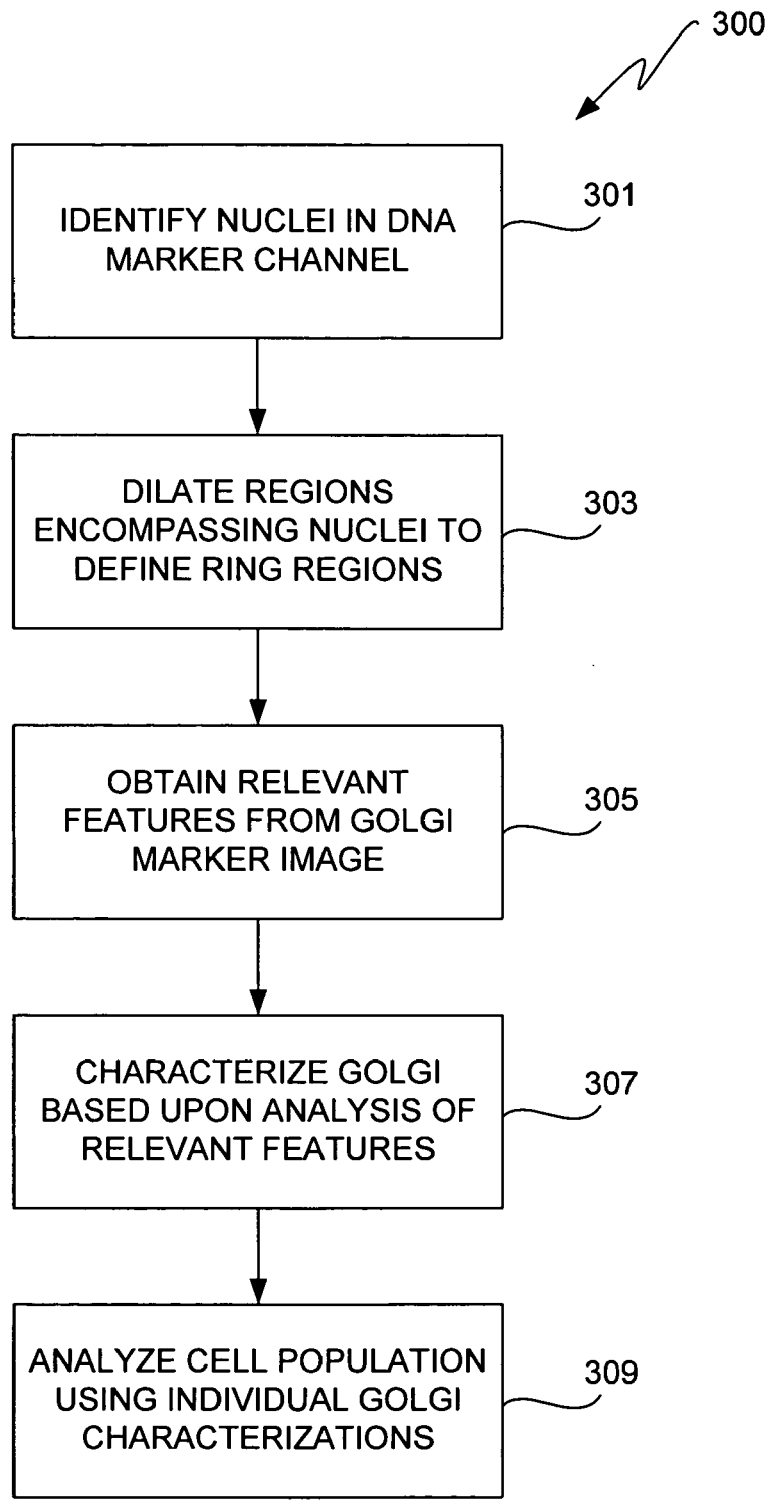
FIG. 3 is a process flow diagram depicting one image analysis process for characterizing Golgi in accordance with this invention.

FIG. 3 depicts a process flow that may be employed to characterize Golgi appearing in images of cells. The process depicted in FIG. 3 (identified by the reference 300) may serve as a combination of algorithms 209 and 211 depicted in FIG. 2, for example.

Initially, the individual cells, or at least the regions of those cells harboring the Golgi complex, are identified. Generally, this process is referred to as "segmentation." This can be accomplished in numerous ways. In the embodiment depicted in FIG. 3, it is accomplished in operations 301 and 303. In this example, the image analysis tool initially identifies the nucleus of each cell captured in the image under consideration. Since images from different channels can be well registrated, nucleus can be first identified in the DNA channel and then overlaid to the image under consideration. Identifying nucleus in the DNA channels may be accomplished using any of a number of nucleus identification/segmentation algorithms. As shown in FIG. 2, the output of nucleus algorithm 209 is provided to Golgi algorithm 211.

After the nuclei have been identified at 301, the Golgi image analysis routine next defines a "ring region" around each nucleus. See 303. Generally, this step serves to define the perinuclear region. It will be described in detail with reference to FIGS. 4A and 4B. For now, it sufficient to understand that the purpose of operation 303 is to define a region that will encompass or subsume some or all of the Golgi complex in a normal interphase cell.

Within the regions defined in operation 303, the features of the Golgi complex may be identified using intensity versus position data. For example, each pixel in the ring region is associated with a particular intensity, at the channel in which the Golgi complex is imaged. From such intensity data, various morphological and/or statistical features may be extracted in order to characterize the Golgi complex. See 305. These features will be described in more detail below. In one particularly interesting embodiment, the features of interest include kurtosis, standard deviation, mean, and singular value decomposition, all obtained from the intensities of the pixels in the ring region.

The statistical and morphological features can provide very useful information for characterizing Golgi complex. In themselves, however, these parameters have no biological meaning. In a preferred embodiment, algorithm 300 converts information contained in these parameters to biologically relevant classifications. This operation is depicted in block 307. In a preferred embodiment, operation 307 classifies all cells into one of four primary Golgi states: normal, diffuse, disperse, and diffuse/disperse.

Further biologically relevant information can be obtained by considering an entire population of cells, and their associated Golgi states. Thus, algorithm 300 concludes with an operation 309, in which a population analysis is conducted. In one example, the relative percentages of cells in any of the stages of cell cycle having Golgi in each of the four above-mentioned end states is computed from data on Golgi status and cell cycle stage of each individual cell. Note that statistics of the Golgi status may be computed independently for interphase and mitotic cells.

Segmentation

Figure 4A:
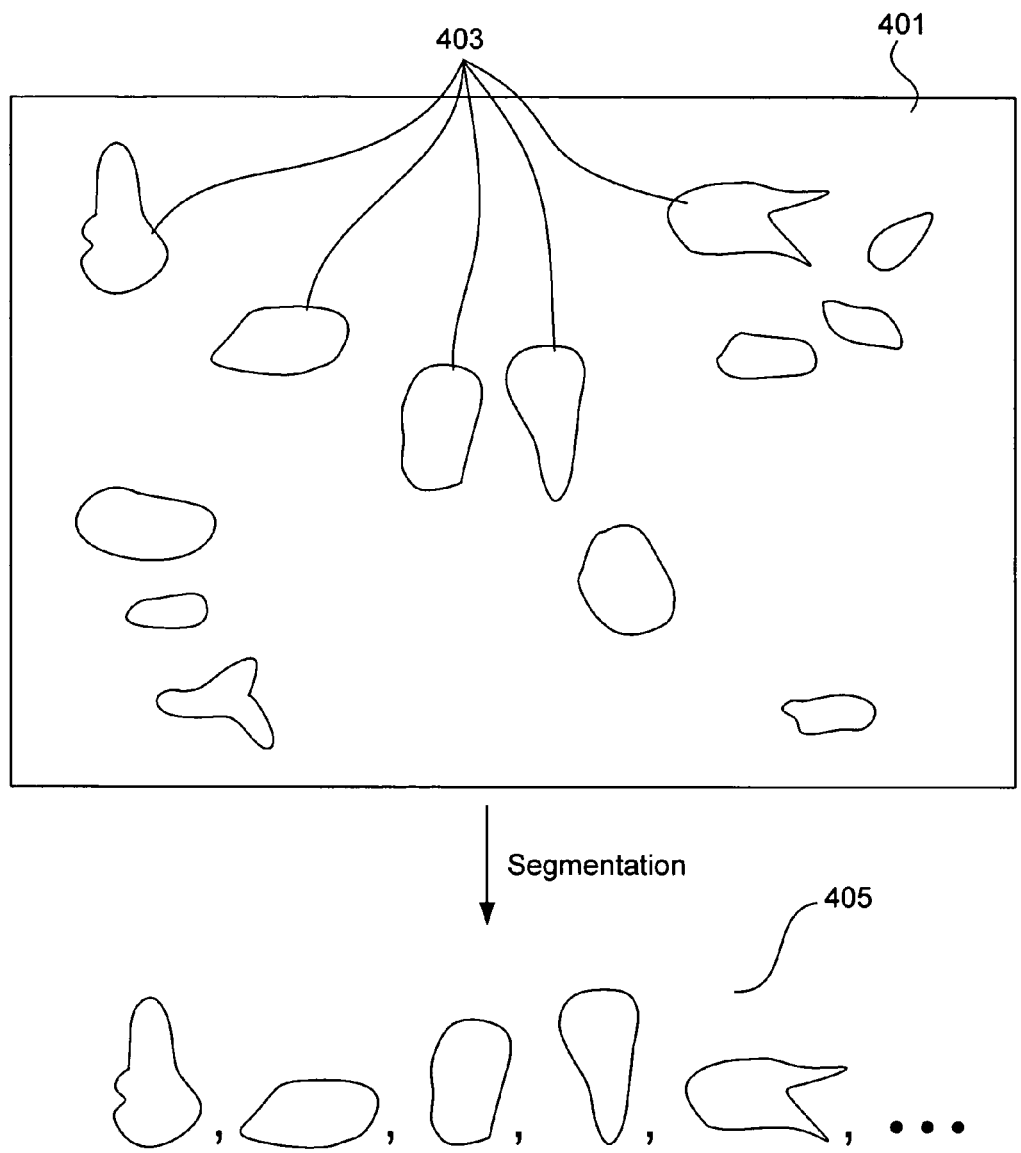
FIG. 4A generally illustrates how an image of multiple cells may be segmented to provide separate representations of individual cells and thereby allow a cell-by-cell analysis.

One approach to segmentation is depicted in FIG. 4A. As shown there, an image 401 includes a plurality of cell nuclei images 403 identified, for example, with a DNA-binding marker. Segmentation effectively converts image 401 into discrete images/representations for the DNA of each cell as shown at 405. In a preferred embodiment, this collection of representation 405 is provided as a mask providing intensity as a function of position for each cell nucleus in image 401.

Individual cell representations 405 may be extracted from image 401 by various image analysis procedures. Preferred approaches include edge finding routines and threshold routines. Some edge finding algorithms identify pixels at locations where intensity is varying rapidly. For threshold routines, pixels contained within the edges will have a higher intensity than pixels outside the edges. Threshold algorithms convert all pixels below a particular intensity value to zero intensity in an image subregion (or the entire image, depending upon the specific algorithm). The threshold value is chosen to discriminate between nuclei images and background. All pixels with intensity values above threshold in a given neighborhood are deemed to belong to a particular cell nucleus.

The concepts underlying thresholding are well known. A threshold value is chosen to extract those features of the image having intensity values deemed to correspond to actual cells (nuclei). Typically an image will contain various peaks, each having collections of pixels with intensity values above the threshold. Each of the peaks is deemed to be a separate "cell" or "nucleus" for extraction during segmentation.

An appropriate threshold may be calculated by various techniques. In a specific embodiment, the threshold value is chosen as the mode (highest value) of a contrast histogram. In this technique, a contrast is computed for every pixel in the image. The contrast may be computed as the intensity difference between a pixel and its neighbors. Next, for each intensity value (0–255 in an eight byte image), the average contrast over all pixels in the image is computed. The contrast histogram provides average contrast as a function of intensity. The threshold is chosen as the intensity value having the largest contrast. See "The Image Processing Handbook," Third Edition, John C. Russ 1999 CRC Press LLC IEEE Press, and "A Survey of Thresholding Techniques," P. K. Sahoo, S. Soltani and A. K. C. Wong, Computer Vision, Graphics, and Image Processing 41, 233–260 (1988), both of which are incorporated herein by reference for all purposes.

In another specific embodiment, edge detection may involve convolving images with the Laplacian of a Guassian filter. The operation performed on the image is given by $$f(x,y) = \int\int I(x-u, y-v)g(u,v)dudv$$

Here I is the intensity of a pixel, x and y are the coordinates in the original image, and g is the Laplacian of a Guassian filter $$\frac{x^2+y^2-2\sigma^2}{2\pi\sigma^8} e^{\frac{x^2+y^2}{2\sigma^2}}.$$

Figure 4B:
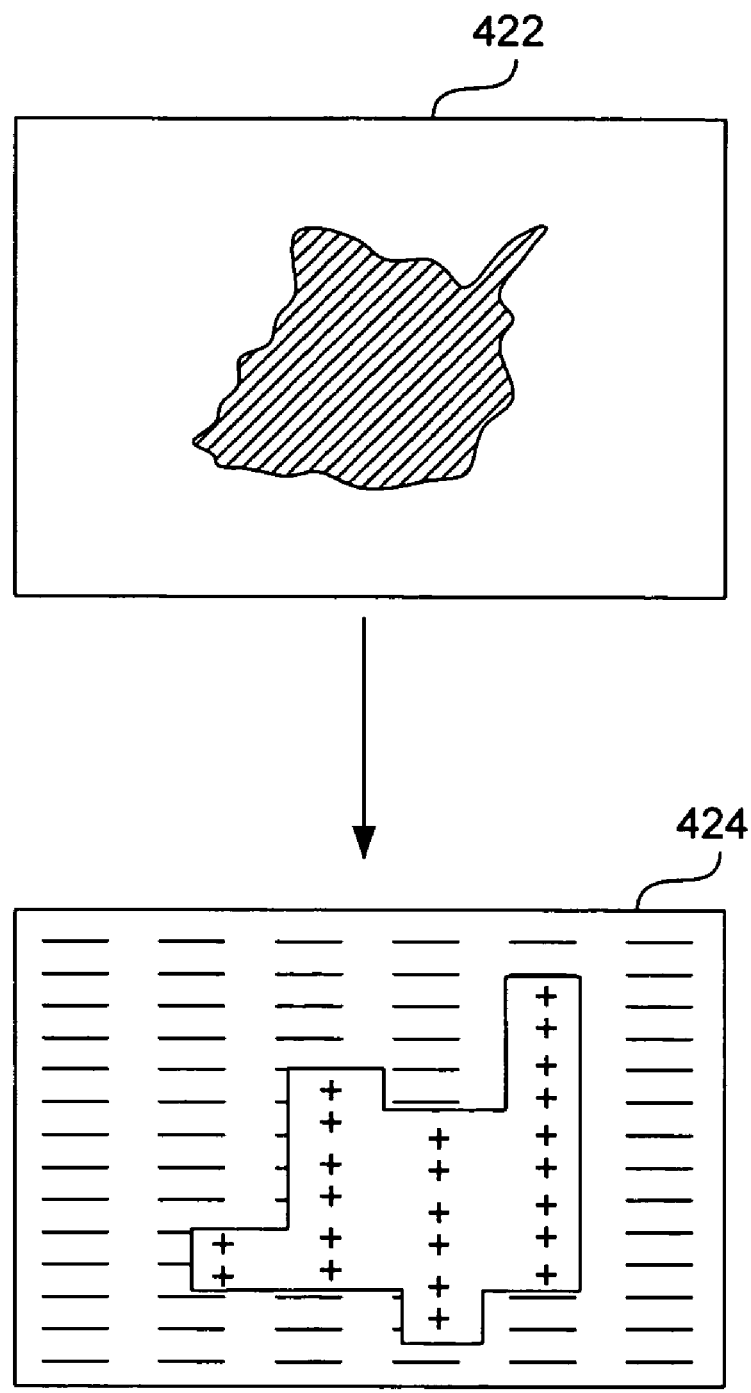
FIG. 4B generally depicts a representation of a cell as a binary object as identified using an edge finding routine.

The zero-crossings of the resulting image f(x,y) are detected as edge points. The edge points are linked to form closed contours, thereby segmenting the relevant image objects. See The Image Processing Handbook, referenced above. FIG. 4B depicts the transformation in a very course fashion. An original image 422 is convolved with the Laplacian of a Guassian filter to give a new image 424 which contains positive and negative values at the component pixels. Note that this figure shows the mask of an object, not detected edges/contours. Wherever the sign changes in moving from one pixel to the next a contour results.

Generation of Ring Region

As indicated in the discussion of 3, it is often desirable to generate a ring about the cell nucleus (see block 303) in order to define a region where normal Golgi are likely to reside. This operation is depicted in cartoon fashion in FIG. 5A. As shown there, an image of a cell's nucleus 503 is bounded by a ring region 505. Within ring region 505, a normal Golgi organelle 507 appears in the image. As explained above, normal Golgi typically reside in the perinuclear region, which is coextensive with ring region 505.

Note that the size of the ring region can be chosen to allow some or all of the normal Golgi to be subsumed. In a preferred embodiment, the size of ring region 505 is chosen to subsume all of the normal Golgi in a majority of interphase cells 507. Diffuse and dispersed Golgi typically are not confined to a perinuclear region. Therefore, ring region 505 may not, depending upon the ring width setting, subsume all the Golgi in these states. The algorithm can use this fact to distinguish, or help distinguish, normal Golgi from diffuse and dispersed Golgi. Assuming that the total "quantity of Golgi" is approximately consistent across normal, diffuse, and disperse states, then the "amount of Golgi" located within ring region 505 will be greatest in the case of the normal Golgi state. Because some significant fraction of the Golgi lies outside of ring region 505 in the case of diffuse and/or disperse Golgi states, the total amount of Golgi detected within region 505 will be less in these states. In preferred embodiments, this is not the primary method used to deduce the Golgi state. Other features of pixel distributions (described below) are used more typically.

Figures 5A, 5B:
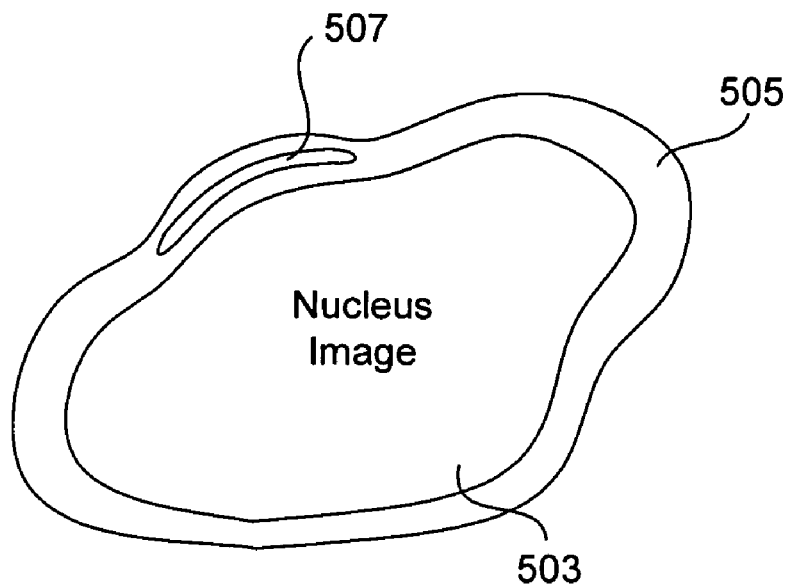
FIGS. 5A and 5B depict a technique for "dilating" an image of a nucleus to create a perinuclear ring region where normal Golgi tend to localize.

The ring shaped region about the nucleus may be defined using various techniques. One suitable technique is depicted in FIG. 5B. As shown there, an image segment 511 comprises a two-dimensional collection of locations or pixels. Each of these is represented by a small rectangular box. The pixels where the nucleus resides are shown with the reference letter "N." To define the ring region, the algorithm locates the nearest neighbor pixels about the edge of the nucleus. In one embodiment, this is accomplished by identifying the four nearest neighbor pixels for each pixel identified as belonging to the nucleus. Those neighboring pixels which themselves form part of the nucleus are not considered. In FIG. 5B, these nearest neighbor pixels are identified by the reference letter "X." To provide the appropriate width for the ring region, this process may be repeated any number of times. In the example shown in FIG. 5B, it is repeated once-to provide a total of two iterations. In the second iteration, each of the pixels considered in the first iteration is used to identify four nearest neighbors. In FIG. 5B, the second iteration nearest neighbors are identified by the reference letter "O."

The exact number of iterations used to define the ring region can vary depending upon the number of parameters. First, one must decide whether the ring region should subsume only Golgi residing in the close perinuclear region or should subsume Golgi residing within a wider portion of the cell, or even the entire cell itself. Second, the desired width of the ring region may vary depending upon the magnification of the image, the resolution of the image, and other related properties of the image.

Note that the mechanism depicted in FIG. 5B represents but a single approach to defining the ring region. Some other suitable techniques will be readily apparent to those of skill in the art. Further, other techniques may be employed to define the region within which the Golgi may be subsumed. For example, some techniques will not consider the DNA or nucleus of a cell. Rather, they will simply focus on the image of the pertinent Golgi component and then consider appropriate morphological and/or statistical parameters to distinguish the Golgi of one cell from the Golgi of another cell. Still further, other techniques will consider other non-Golgi features of an image to distinguish one cell from another. For example, some algorithms may distinguish cells based upon images of the plasma membrane, cytoskeleton, etc. U.S. patent application Ser. No. 09/792,013 previously incorporated by reference, describes a technique that uses tubulin (or other cytoskeletal component) and DNA markers together to identify discrete cells. Regardless of which technique is employed, in the end, regions subsuming some or all of the Golgi within discrete cells must be separately identified. Then, the image of the appropriate Golgi marker can be analyzed to characterize the Golgi in accordance with this invention. Note that while separate analysis of Golgi regions in each individual cell is often preferable, this is not a necessary requirement of the algorithm. Upon creation of "ring" areas, all pixels in all of the rings can be analyzed simultaneously.

Relevant Golgi Features

In order to effectively characterize the Golgi complex of individual cells, the present invention may make use of various parameters derived from Golgi complex images. These parameters may represent the shape, size, concentration, texture, and amount of Golgi components in an individual cell. In one preferred algorithm of the present invention, one set of parameters is used to characterize the "type" of Golgi and another parameter or set of parameters is used to characterize the amount of Golgi complex in an individual cell. The types of Golgi may include normal, diffuse, disperse, and disperse/diffuse as discussed above. Of course, other suitable processes may consider different and/or additional types of Golgi. The amount of Golgi may be determined from the local concentrations of a marked Golgi component summed over the entire region of interest (e.g. a ring region).

Note that while the discussion below is organized sequentially, the described features of different nature may be used simultaneously to classify Golgi states. The parameters chosen for use with this invention should allow discrimination between biologically relevant classifications. Further, they may provide a continuous measure of the degree to which an individual cell exhibits features of any of the classifications. As mentioned, particularly interesting parameters will relate to one or more of the following general features of the Golgi complex image: the shape (such as peakedness) of an intensity (marker concentration) histogram, the texture of the Golgi areas, the overall intensity (some of local marker concentrations) of the Golgi image, and the moment (including moments of different orders) of the Golgi complex about the nucleus. Another set of features for the Golgi complex are statistics computed from a histogram of the intensity of pixel intensities by angle from the center of the nuclei. The x-axis of this histogram is the angle of the vector connecting the center of the nuclei to the ring pixel. The y-axis is the sum of the pixel intensities at a given angle. When the histogram is unimodal the Golgi complex is likely classified as normal, if the histogram has many modes the Golgi complex is likely classified as dispersed and if the histogram is uniform the Golgi complex is likely classified as diffuse.

Figure 6:
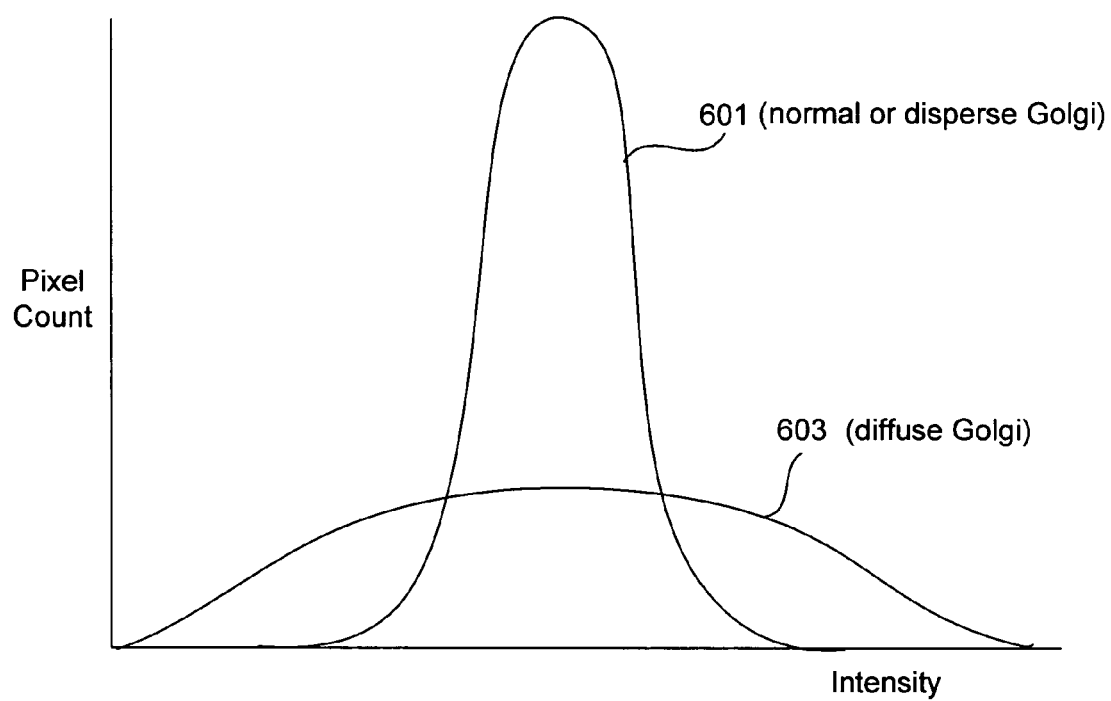
FIG. 6 is an intensity histogram showing peaked and flat curves corresponding to normal and diffuse Golgi, respectively.

Regarding peakedness, FIG. 6 depicts sample histograms for normal and diffuse Golgi. As shown in FIG. 6, a histogram plots the pixel count (number of pixels in an image meeting a criteria) as a function of pixel intensity. Remember that the intensity is a measure of the local concentration of a marked component in the Golgi complex. A Golgi complex with high local concentrations of the marked Golgi component will have a narrow intensity distribution as shown by curve 601. A diffuse Golgi complex will have a wider distribution as illustrated by curve 603.

Generally, normal Golgi, and to some degree dispersed Golgi, possess local regions of high concentration of marked Golgi component. Therefore, these types of Golgi will have histograms with relatively narrow distributions. In contrast, diffuse Golgi complexes have their marked components relatively evenly distributed throughout most or all of the ring area. Therefore, the histogram of such diffuse Golgi will have a relatively wide distribution. In FIG. 6, curve 601 might represent the histogram of normal or dispersed Golgi, while curve 603 might represent a histogram of diffuse Golgi.

Another parameter of interest in characterizing Golgi is the texture. The texture may be characterized by a number of parameters such as the singular value decomposition of a matrix of intensity values representing the marked Golgi component. Generally the texture of an object relates to the size and shape of the granules or other components of an image. Various texture related features can help to discriminate between normal and dispersed Golgi and/or between dispersed and diffuse/dispersed states.

Figure 7:
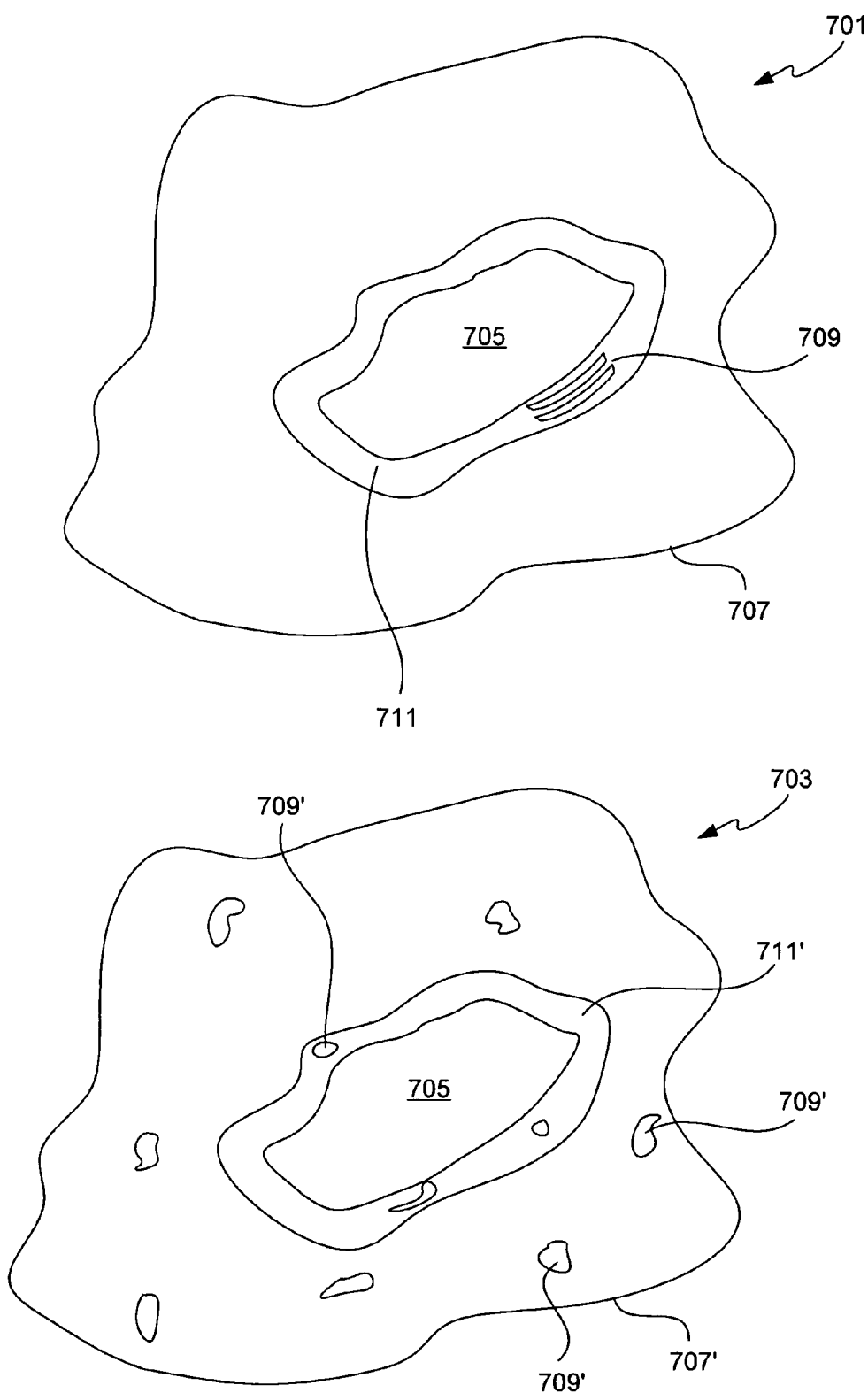
FIG. 7 is a cartoon depiction of cellular Golgi showing how normal and dispersed Golgi segregate inside and outside the perinuclear region, respectively.

The overall intensity associated with an image of the Golgi complex can represent the total amount of particular Golgi component(s) within a given cell or region of a cell. FIG. 7 illustrates how this concept can be used to distinguish between normal Golgi and dispersed Golgi using an algorithm that employs a ring region as described above. As shown in FIG. 7, a cell 701 possesses normal Golgi while a cell 703 possesses dispersed Golgi. Each cell includes a nucleus 705 and a plasma membrane 707. In the case of cell 701, the Golgi complex (represented by reference number 709) resides entirely within a ring region 711. In this cell, all of its Golgi resides within ring region 711. Therefore, the total intensity of a Golgi marker found within ring region 711 will represent all of the Golgi in cell 701. In contrast, cell 703 has a comparable ring region 711' which subsumes only a fraction of the Golgi in that cell (709'). The remainder of the dispersed Golgi lies outside the ring region 711'. As a consequence, it may be expected that the total intensity of Golgi calculated for cell 703 (using ring region 711') will be less than the total intensity calculated for cell 701.

The biologically relevant features of the Golgi complex may be obtained from various mathematical parameters. Among the parameters of interest are the following: the total area of the ring region in which the Golgi marker is considered, the mean intensity of all pixels in the ring region, the standard deviation of the pixel intensities in ring region, the kurtosis of the pixel intensities in the ring region, and the second, third, and fourth largest eigenvalues obtained by a singular value decomposition of a matrix of pixels in the ring. Also, sometimes, the Golgi "type" (normal, diffuse, dispersed, or diffuse and dispersed) is treated as a parameter. This is technically a characterization derived from parameters such as the SVD eigenvalues, the kurtosis, etc. In a particularly preferred embodiment, the following four relevant parameters are used to characterize the Golgi complex: mean, standard deviation, kurtosis, and singular value decomposition.

Singular value decomposition and kurtosis can be derived from digitized images using conventional approaches. Kurtosis is given by $m_4/(std)^4$, where std is the standard deviation of intensity of the pixels in the ring region in the image and $m_4$ is given by the following expression:

$$m_4 = \frac{1}{N}\sum_{i=1}^{N}(x_i - \tilde{x})^4$$

In this expression, N is the number of pixels in the ring region in the image, $x_i$ is the pixel intensity, and $\tilde{x}$ is the mean pixel intensity. The kurtosis is particularly useful in distinguishing diffuse Golgi from normal or dispersed Golgi. Particularly, higher values of kurtosis suggest a higher degree of the Golgi "diffusion."

The singular value decomposition is technique that operates on a matrix of pixel intensity values arranged in their relative spatial positions as in the image. Preferably, these pixel intensities are obtained from a ring region as described above. The relevant values are obtained by multiplying the matrix with its transpose and obtaining the eigenvalues. The singular value decomposition provides information about the texture of the Golgi complex in the image. Thus, it is useful in distinguishing different states of the Golgi complex.

One aspect of the present invention is the ability to estimate the amount of Golgi (or a component of the Golgi) in a given cell or region of a cell. This allows one to characterize cells based upon relative or absolute quantity of a particular Golgi component within some region of the cell such as the perinuclear region. In general, an agent applied to highlight Golgi should emit a signal that is proportional to the amount of agent that has bound to a Golgi component. Thus, the amount of signal (usually indicated by the signal intensity summed or integrated over the entire region of interest) provides a direct indication of the quantity of a Golgi component present. When this is the case, the present invention allows one to obtain an accurate measure of the amount of Golgi in a given cell or cell region.

Techniques for estimating the quantity of DNA in a cell nucleus are described U.S. patent application Ser. No.

09/729,754, previously incorporated by reference. These techniques may involve subtracting background signal and other image processing procedures. In general, such techniques apply to estimating the quantity of Golgi in a cell or region of a cell.

Classification of Golgi

Optionally, the algorithms of this invention may specifically classify the Golgi complex into one or more biologically relevant classification based upon parameters such as those described above. As mentioned previously, one example of biologically relevant classifications include the four classifications depicted in FIGS. 1A–1D. In the context of the general process flow depicted in FIG. 3, the biologically relevant classification takes place at block 307. This operation takes as its inputs morphological, textual, and/or statistical parameters and provides as an output the biological relevant classifications. It accomplishes this using an appropriate model provided in the form of a neural network, linear or non-linear mathematical expression, a tree or graph, and the like. As previously, mentioned, one preferred approach employs a classification and regression tree.

Figure 8:
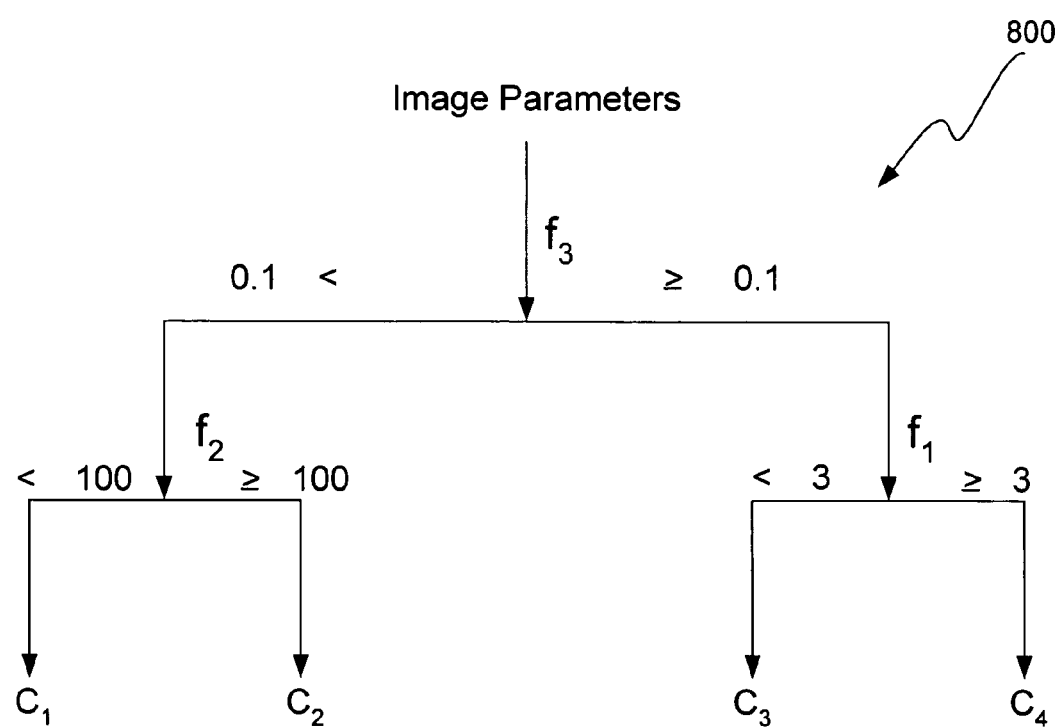
FIG. 8 is a sample classification and regression tree of the type that may be employed to classify Golgi in accordance with this invention.

Classification and regression trees (CART) are well known tools for classifying objects. They are described in Brieman et al., (1984) Classification and Regression Trees. Monterey: Wadswirth and Brooks/Cole. FIG. 8 depicts one example of a classification and regression tree (CART) 800. In this example, there are three input parameters and four possible classifications. The input parameters are identified as, $f_1$, $f_2$, and $f_3$. The classifications are denoted $C_1$, $C_2$, $C_3$, and $C_4$. In this hypothetical example, the tree initially considers the input parameter $f_3$. If the value of $f_3$ is less than 0.1, the tree branches in one direction. If, on the other hand, the value of $f_3$ is greater than or equal to 0.1, the tree branches in the opposite direction. Assuming that the value of $f_3$ is less than 0.1, the tree next requires that the parameter $f_2$ be considered. In this example, if the value of $f_2$ is less than 100, the model classifies the Golgi complex in $C_1$. On the other hand, if the value of $f_2$ is greater than or equal to 100 the model classifies the Golgi complex in $C_2$. Similarly, if the value of $f_3$ is found to be greater than or equal to 0.1, then the value of the input parameter $f_1$ is considered. Should the value of $f_1$ be less than 3, the tree classifies the Golgi complex in $C_3$. Finally, if the value of $f_1$ is found to be greater than or equal to 3, then the model classifies the Golgi complex in $C_4$.

Obviously, the parameters $f_1$, $f_2$, and $f_3$ will be relevant to classification of Golgi, in accordance with this invention. For example, $f_1$ might correspond to the mean pixel intensity of the Golgi channel, $f_2$ might correspond to the standard deviation of the pixel intensity values of the Golgi channel, and $f_3$ might correspond to the second, third, and/or fourth singular value decomposition of a matrix of pixel intensity values in the ring region. The classification $C_1$ through $C_4$ might correspond to the Golgi complex states depicted in FIGS. 1A through 1D.

Classification models may be generated using numerous techniques. These include regression analyses (e.g., techniques for generating CARTs), neural networks, maximum likelihood/mixture models, etc. In general, any model requires a valid training set containing numerous samples that span the range of likely cases that will be encountered in practice. The samples should span a wide range of classification types, including types that vary in degree between extreme end cases (e.g., the diffuse/disperse Golgi state). In addition, the samples should include a wide range of input parameters. Each sample will have an ascribed classification and clearly defined input parameters. In this case, it will typically be necessary for an experienced scientist to classify images based upon their Golgi state. These classifications together with the relevant parameters (e.g. mean, standard deviation, kurtosis, and singular value decompositions) are provided to a tool for generating the appropriate classification model.

To maximize the predictive accuracy of the model, it may be appropriate to generate separate models for specific ranges of conditions. Typically, a separate model will be generated for each different cell line to be considered, because the appearance of the Golgi complex varies widely from cell line to cell line. Further, settings associated with the image analysis apparatus may cause significant variations in the image analysis. Therefore, separate models may be appropriate for different image analysis settings such as magnification, illumination intensity and the like. As noted, the Golgi complex may be imaged using various components contained within the Golgi complex. For example, some components may be detected with labeled lectins and other markers may be detected with labeled antibodies. Each of these separate component-marker combinations may deserve its own model, assuming more than one marker is used for the Golgi complex.

As indicated above, certain embodiments of the invention do not necessarily employ a classification operation. In these embodiments, the algorithm simply employs the parameters generated a block 305 in order to draw conclusions about a population of cells. Or alternatively the analysis tool may generate coefficients for biologically relevant features such as diffusion. In one example, the kurtosis of the Golgi image (or some derivation from kurtosis) serves as a coefficient for diffusion. Further, the system could output both the biologically relevant classification of end states and the particular parameters used to generate these classifications.

Analysis of Populations of Cells

As mentioned, the most useful biological information often comes from images of a population of cells. The population may comprise a very limited range of variations, such as a single cell treated with a single drug at a single concentration. Or it may comprise a diverse set of variations such as multiple cell lines, each treated with multiple concentrations of a drug (or even multiple drugs believed to operate via a single mechanism of action).

Note that many images used with the present invention will contain many discrete cells. The images often show several hundreds of cells, although the actual number depends on the application. Such cells may collectively comprise the population of interest. Or multiple wells or a subset of a single well may comprise the population.

Regardless of how the population is defined, it should preferably contain a relevant sample of cells exposed to a condition of interest. From this population, conclusions about a given stimulus' effect on the Golgi complex can be drawn. The Golgi complex in the population can be characterized by the percent of cells in each primary category of Golgi end state or by a distribution of Golgi specific parameters across the population or by some other measure of Golgi parameters and/or classes across the population. As mentioned, interphase cells typically hold the most relevant information about an effect of a stimulus on the Golgi complex. This is because unperturbed interphase cells typically have normal Golgi of the type depicted in FIG. 1A. Deviations from this normal state, such as illustrated in FIGS. 1B, 1C, and 1D, provide clues about the effect of a stimulus. Mitotic cells, in contrast, do not exhibit the "normal" Golgi state even in the absence of an additional stimulus and instead exhibit the diffuse and/or disperse state.

Therefore, it is useful to characterize cells based on their position in the cell cycle—at least as either mitotic or interphase.

As explained in U.S. patent application Ser. No. 09/729,754, previously incorporated by reference, an image of a cells nucleus (DNA) can be analyzed to distinguish between the $G_1$, S, and $G_2$, and M phases of a cell. Briefly, the total amount of DNA in a cell nucleus can indicate whether an interphase cell is in the $G_1$, S, or $G_2$ phase. Another parameter or grouping of parameters can discriminate between mitotic and interphase cells. One example of such parameter is the variance in intensity exhibited by an indicator of DNA concentration. One example of a group of parameters is average pixel intensity and area of the nucleus. In this second example, the average pixel intensity is the average of the pixel-based intensities of the nucleus and "area" is the total area of the nucleus.

In a particularly preferred embodiment, the cells of a population are first characterized using marked DNA. This classification at least distinguishes between mitotic and interphase cells. Then, the same cells are characterized using marked Golgi. Particular attention is paid to the Golgi complex of the interphase cells.

Software/Hardware

Generally, embodiments of the present invention employ various processes involving data stored in or transferred through one or more computer systems. Embodiments of the present invention also relate to an apparatus for performing these operations. This apparatus may be specially constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines will appear from the description given below.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). The data and program instructions of this invention may also be embodied on a carrier wave or other transport medium. Examples of program instructions include both machine code, such as produced by a compiler, and files containing higher level code that may be executed by the computer using an interpreter.

Figure 9:
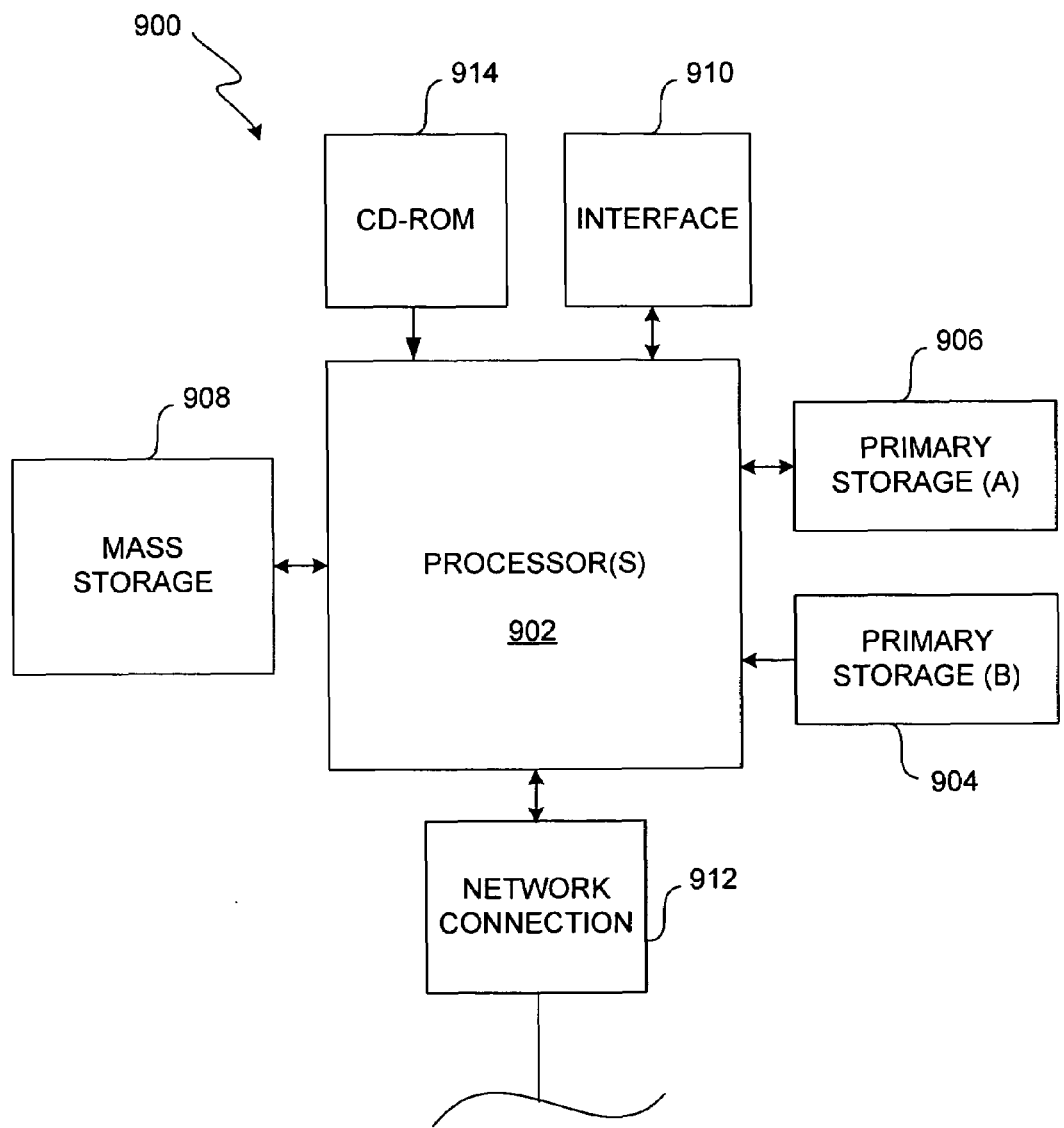
FIG. 9 is a block diagram of a computer system that may be used to implement various aspects of this invention such as the various image analysis algorithms of this invention.

FIG. 9 illustrates a typical computer system that, when appropriately configured or designed, can serve as an image analysis apparatus of this invention. The computer system 900 includes any number of processors 902 (also referred to as central processing units, or CPUs) that are coupled to storage devices including primary storage 906 (typically a random access memory, or RAM), primary storage 904 (typically a read only memory, or ROM). CPU 902 may be of various types including microcontrollers and microprocessors such as programmable devices (e.g., CPLDs and FPGAs) and unprogrammable devices such as gate array ASICs or general purpose microprocessors. As is well known in the art, primary storage 904 acts to transfer data and instructions uni-directionally to the CPU and primary storage 906 is used typically to transfer data and instructions in a bi-directional manner. Both of these primary storage devices may include any suitable computer-readable media such as those described above. A mass storage device 908 is also coupled bi-directionally to CPU 902 and provides additional data storage capacity and may include any of the computer-readable media described above. Mass storage device 908 may be used to store programs, data and the like and is typically a secondary storage medium such as a hard disk. It will be appreciated that the information retained within the mass storage device 908, may, in appropriate cases, be incorporated in standard fashion as part of primary storage 906 as virtual memory. A specific mass storage device such as a CD-ROM 914 may also pass data unidirectionally to the CPU.

CPU 902 is also coupled to an interface 910 that connects to one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 902 optionally may be coupled to an external device such as a database or a computer or telecommunications network using an external connection as shown generally at 912. With such a connection, it is contemplated that the CPU might receive information from the network, or might output information to the network in the course of performing the method steps described herein.

In one embodiment, the computer system 900 is directly coupled to an image acquisition system such as an optical imaging system that captures images of cells. Digital images from the image generating system are provided via interface 912 for image analysis by system 900. Alternatively, the images processed by system 900 are provided from an image storage source such as a database or other repository of cell images. Again, the images are provided via interface 912. Once in the image analysis apparatus 900, a memory device such as primary storage 906 or mass storage 908 buffers or stores, at least temporarily, digital images of the cell. Typically, the cell images will show locations where Golgi, and possibly DNA, exists within the cells. In these images, local values of a Golgi image parameter (e.g., radiation intensity) correspond to amounts of a Golgi component at the locations within the cell shown on the image. With this data, the image analysis apparatus 900 can perform various image analysis operations such as distinguishing between normal and diffuse and/or dispersed Golgi and estimating the amount of Golgi in a cell. To this end, the processor may perform various operations on the stored digital image. For example, it may analyze the image in manner that extracts values of one or more Golgi state parameters that correspond to a Golgi primary state and classifies the cell as either normal of diffuse, disperse or diffuse/disperse based upon the extracted values of the parameters. Alternatively, or in addition, it may estimate a total value of the Golgi image parameter taken over at least a perinuclear region of the cell.

EXAMPLES

The following examples each involved generation and analysis of images obtained from SKOV3 cells treated with a Lens culinaris lectin marker. The cells were incubated with each drug for 24 hours before fixation and staining. In each case, ring regions were obtained by the Golgi segmentation algorithm described above. In addition, the Golgi complex within those ring regions was predicted, using a CART model as described above, as either normal, diffuse, dispersed, or diffuse and dispersed.

In a first example, SKOV3 cells that were treated with a low concentration (0.6 nanomolar) of the anti-microtubule drug Taxol. In this example, the Golgi complex remains normal as determined by the model. An expert independently examined the images and concluded that the Golgi complex was normal. In a second example, SKOV3 cells treated with a high concentration (2.6 micromolar) of microtubule-de polymerizing drug Nocodazole. Using the same model, the Golgi complex was found to be dispersed. And the expert independently confirmed that the Golgi complex was in fact dispersed. Finally, in a third example, SKOV3 cells were treated with a drug that disrupts transport into and out of the Golgi complex—Brefeldin A. The drug was provided in a concentration of 79 micromolar. In this case, the image analysis algorithm classified the Golgi complex as diffuse. The expert independently confirmed this.

Conclusion

Although the above has generally described the present invention according to specific processes and apparatus, the present invention has a much broader range of applicability. In particular, the present invention is not limited to a particular kind of cell component, not just the Golgi complex. Thus, in some embodiments, the techniques of the present invention could provide information about many different types or groups of cellular organelles and components of all kinds. Of course, one of ordinary skill in the art would recognize other variations, modifications, and alternatives.

What is claimed is:

1. A method, implemented on a computing device, of analyzing an image of one or_more cells, the method comprising:
   (a) identifying a region of the image subsuming some or all of the Golgi complex of a single cell;
   (b) within said region, automatically identifying the location of the Golgi complex;
   (c) based upon at least one of (i) the Golgi complex location within the region and (ii) the Golgi concentration within the region, automatically mathematically characterizing the Golgi complex within the single cell by calculating one or more of the kurtosis of intensity values associated with Golgi complex, an eigenvalue of a singular value decomposition of intensity values associated with Golgi complex, a mean of intensity values associated with Golgi complex, and a standard deviation of intensity values associated with Golgi complex; and
   (d) applying the mathematical characterization to a Golgi classification model to thereby automatically classify the Golgi complex in a category that at least partially distinguishes between normal Golgi and Golgi that is either diffuse or disperse or both diffuse and disperse.

2. The method of claim 1, wherein the image comprises multiple cells, and wherein identifying the region of the image subsuming some or all of the Golgi complex comprises segmenting the image into regions, each subsuming at least part of an individual cell.

3. The method of claim 2, wherein segmenting comprises identifying locations of nuclei in the cells.

4. The method of claim 3, wherein the nuclei are identified by identifying regions of the image where DNA is shown to concentrate.

5. The method of claim 3, further comprising within the image dilating the locations of the nuclei to subsume the locations of some or all of the Golgi complex in the individual cells.

6. The method of claim 1, wherein the image depicts concentration versus position of one or more Golgi components within the cell.

7. The method of claim 6, wherein the concentration of at least one Golgi component corresponds to intensity in the image.

8. The method of claim 1, wherein one or more cells in the image were treated with a material that binds to a component of the Golgi complex and emits a signal having an intensity corresponding to its concentration.

9. The method of claim 8 wherein the material is a lectin or antibody that binds to the component of the Golgi complex.

10. The method of claim 1, wherein the mathematical characterization of the Golgi complex comprises at least one of (i) an indicator of the peakedness of a histogram of at least one component of the Golgi complex, (ii) the texture of the Golgi complex and (iii) and the amount of Golgi complex in the region.

11. The method of claim 1, wherein the mathematical characterization of the Golgi complex comprises at least one of a mean and a standard deviation of intensity values obtained from the image.

12. The method of any one of claims 1 or 11, wherein the intensity values correspond to local concentrations of a component of the Golgi complex within the single cell.

13. The method of claim 1, wherein classifying the Golgi complex comprises analyzing the mathematical characterization with a biological model of the Golgi complex.

14. The method of claim 13, wherein the biological model is a regression model or a neural network.

15. The method of claim 13, wherein the biological model is a classification and regression tree.

16. The method of claim 1, further comprising characterizing a population of cells from the image by considering the category of Golgi complex in each cell of the population.

17. The method of claim 16, further comprising predicting a mechanism of action from the characterization of the population.

18. A computer program product stored on a computer readable medium and comprising program instructions for analyzing an image of one or more cells, the program instructions comprising:
   (a) program code for identifying a region of the image subsuming some or all of the Golgi complex of a single cell;
   (b) program code for automatically identifying, within said region, the location of the Golgi complex;
   (c) program code for using at least one of (i) the Golgi complex location within the region and (ii) the Golgi concentration within the region, to automatically mathematically characterize the Golgi complex within the single cell by calculating one or more of the kurtosis of intensity values obtained from the image, an eigenvalue of a singular value decomposition of intensity values associated with Golgi complex, (c) a mean of intensity values associated with Golgi complex, (d) a standard deviation of intensity values associated with Golgi complex; and (d) program code for applying the mathematical characterization to a Golgi classification model to thereby automatically classify the Golgi complex in a category that at least partially distinguishes between normal Golgi and Golgi that is either diffuse or disperse or both diffuse and disperse.

19. The computer program product of claim 18, wherein the image comprises multiple cells, and wherein the program code for identifying the region of the image subsuming some or all of the Golgi complex comprises program code for segmenting the image into regions, each subsuming at least part of an individual cell.

20. The computer program product of claim 19, wherein the program code for segmenting comprises program code for identifying locations of nuclei in the cells.

21. The computer program product of claim 20, wherein the program code for identifying locations of nuclei comprises program code for identifying regions of the image where DNA is shown to concentrate.

22. The computer program product of claim 20, further comprising program code for dilating the locations of the nuclei within the image to subsume the locations of some or all of the Golgi complex in the individual cells.

23. The computer program product of claim 18, wherein the image depicts concentration versus position of one or more Golgi components within the cell.

24. The computer program product of claim 18, wherein the mathematical characterization of the Golgi complex comprises at least one of (i) an indicator of the peakedness of a histogram of at least one component of the Golgi complex, (ii) the texture of the Golgi complex and (iii) and the amount of Golgi complex in the region.

25. The computer program product of claim 18, wherein the program code for classifying the Golgi complex comprises program code for analyzing the mathematical characterization with a biological model of the Golgi complex.

26. The computer program product of claim 25, wherein the biological model is a regression model or a neural network.

27. The computer program product of claim 25, wherein the biological model is a classification and regression tree.

28. The computer program product of claim 18, further comprising program code for characterizing a population of cells from the image by considering the category of Golgi complex in each cell of the population.

29. The computer program product of claim 28, further comprising program code for predicting a mechanism of action from the characterization of the population.

30. An apparatus for automatically analyzing an image of one or more cells, the apparatus comprising:
an interface configured to receive the image of one or more cells;
a memory for storing, at least temporarily, some or all of the image; and
one or more processors in communication with the memory and designed or configured to segment the image into discrete regions, each subsuming some or all of the Golgi complex in single cell; mathematically characterize the Golgi complex of single cells by calculating one or more of (a) a kurtosis of intensity values obtained from the image, (b) an eigenvalue of a singular value decomposition of intensity values associated with Golgi complex, (c) a mean of intensity values associated with Golgi complex, (d) a standard deviation of intensity values associated with Golgi complex; and apply the mathematical characterization to a Golgi classification model to thereby automatically classify the Golgi complex in a category that at least partially distinguishes between normal Golgi and Golgi that is diffuse or disperse.

31. The apparatus of claim 30, wherein the one or more processors classifies the Golgi complex by using a biological model.

32. The apparatus of claim 31, wherein the biological model is a classification and regression tree.

33. The apparatus of claim 30, wherein the one or more processors segment the image by first identifying regions of the image corresponding to nuclei of the one or more cells.

34. The apparatus of claim 33, wherein the one or more processors perform a dilation operation at the regions of the nuclei on the image in order to subsume the Golgi complex of each of the one or more cells.

35. The apparatus of claim 30, wherein the image to be received by the interface depicts concentration versus position of one or more Golgi components within the cell.

36. The apparatus of claim 35, wherein the one or more Golgi components correspond to intensity values in the image to be received by the interface.

37. The apparatus of claim 30, wherein the one or more cells in the image were treated with a material that binds to a component of the Golgi complex and emits a signal having an intensity corresponding to its concentration.

38. The apparatus of claim 30, wherein the one or more processors mathematically characterize the Golgi complex by calculating at least one or (i) an indicator of the peakedness of a histogram of at least one component of the Golgi complex, (ii) the texture of the Golgi complex, and (iii) the amount of Golgi complex in the discrete regions.

39. The apparatus of claim 30, wherein the one or more processors is further designed or configured to characterize a population comprising the one or more cells by considering a category of Golgi for each of the one or more cells.

40. The apparatus of claim 39, wherein the one or more processors is further designed or configured to predict a mechanism of action from characterizing the population.

* * * * *